(12) United States Patent
Zagury

(10) Patent No.: US 12,024,558 B2
(45) Date of Patent: Jul. 2, 2024

(54) METHOD OF INHIBITING HIV-1 VIRAL REBOUND IN A SUBJECT USING INTERFERON INHIBITORS AND ART

(71) Applicant: 21C Bio, Paris (FR)

(72) Inventor: Daniel Zagury, Paris (FR)

(73) Assignee: 21C BIO, Paris (FR)

( * ) Notice: Subject to any disclaimer, the term of this patent is extended or adjusted under 35 U.S.C. 154(b) by 0 days.

(21) Appl. No.: 16/857,715

(22) Filed: Apr. 24, 2020

(65) Prior Publication Data

US 2021/0332127 A1 Oct. 28, 2021

(51) Int. Cl.
*C07K 16/24* (2006.01)
*A61P 31/18* (2006.01)
*C07K 16/28* (2006.01)
*A61K 45/06* (2006.01)

(52) U.S. Cl.
CPC ............ *C07K 16/249* (2013.01); *A61P 31/18* (2018.01); *C07K 16/2866* (2013.01); *A61K 45/06* (2013.01); *C12N 2740/16011* (2013.01)

(58) Field of Classification Search
CPC .................. A61P 31/18; C07K 16/249; C12N 2740/16011
See application file for complete search history.

(56) References Cited

U.S. PATENT DOCUMENTS

2019/0389956 A1 12/2019 Zhang et al.

FOREIGN PATENT DOCUMENTS

| WO | 2016/134202 A1 | 8/2016 |
| WO | 2018/081197 A1 | 5/2018 |
| WO | 2019/075465 A1 | 4/2019 |

OTHER PUBLICATIONS

Chen, C., et al., Sep. 1992, Generation and analysis of random point mutations in an antibody CDR2 sequence: Many mutated antibodies lose their ability to bind antigen, J. Exp. Med. 176:855-866.*
Liu, Z., et al., 1999, Fine mapping of the antigen-antibody binding interaction of scFv215, a recombinant antibody inhibiting RNA polymerase II from *Drosophila melanogaster*, J. Mol. Recog. 12:103-111.*
Xiang, J., et al., 1999, Light-chain framework region residue Tyr71 of chimeric B72.3 antibody plays an important role in influencing the TAG72 antigen binding, Prot. Engineer. 12(5):417-421.*
Chatellier, J., et al., 1996, Functional mapping of conserved residues located at the VL and VH domain interface of a Fab, J. Mol. Biol. 264:1-6.*
Laird, G. M., et al., May 2015, Ex vivo analysis identifies effective HIV-1 latency-reversing drug combinations, J. Clin. Invest. 125(5):1901-1912.*
Bullen, C. K., et al., Apr. 2014, New ex vivo approaches distinguish effective and ineffective single agents for reversing HIV-1 latency in vivo, Nat. Med. 20(4):425-430.*
Rasmussen, T. A., et al., Feb. 2016, Reversal of latency as part of a cure for HIV-1, Trends Microbiol. 24(2):90-97.*
Shan, L., and R. F. Siliciano, 2013, From reactivation of latent HIV-1 to elimination of the latent reservoir: The presence of multiple barriers to viral eradication, Bioessays 35:544-552.*
Marsden, M. D., 2020, Benefits and limitations of humanized mice in HIV persistence studies, Retrovirol. 17(7):1-6.*
Sliva, K., 2015, Latest animal models for anti-HIV drug discovery, Exp. Opin. Drug Discov. 10(2):111-123.*
Ait-Ammar, A., et al., Jan. 2020, Current Status of Latency Reversing Agents Facing the Heterogeneity of HIV-1 Cellular and Tissue Reservoirs, Front. Microbiol. vol. 10, Article 3060, pp. 1-23.*
Vanhamel, J., et al., 2019, Establishment of Latent HIV-1 Reservoirs: What Do We Really Know? J. Virus Evolution 5:3-9.*
Chun, T.-W., et al., Jun. 2015, HIV Reservoirs as Obstacles and Opportunities for an HIV Cure, Nat. Immunol. 16(6):584-589.*
Massanella, M., and D. D. Richman, 2016, Measuring the Latent Reservoir In Vivo, J. Clin. Invest. 126(2):464-472.*
Liang Cheng et al., "Blocking type I interferon signaling enhances T cell recovery and reduces HIV-1 reservoirs", The Journal of Clinical Investigation, Jan. 3, 2017, vol. 127(1), (12 pp.), doi: 10.1172/JCI90745.
Tae-Wook Chun et al., "Durable Control of HIV Infection in the Absence of Antiretroviral Therapy: Opportunities and Obstacles", Journal of the American Medical Association, Jul. 2, 2019, vol. 322(1), pp. 27-28 (2 pp.), doi: 10.1001/jama.2019.5397.
Matthew C. Pitman et al., "Barriers and strategies to achieve a cure for HIV", HHS Public Access Author manuscript, Lancet HIV, Jun. 2018, vol. 5(6), pp. 1-26 (26 pp.), doi: 10.1016/S2352-3018(18)30039-0.
Jeanna B. Honeycutt et al., "HIV persistence in tissue macrophages of humanized myeloid-only mice during antiretroviral therapy", HHS Public Access Author manuscript, Nature Medicine, May 2017, vol. 23(5), pp. 1-16 (16 pp.), doi: 10.1038/nm.4319.
Henintsoa Rabezanahary et al., "Despite early antiretroviral therapy effector memory and follicular helper CD4 T cells are major reservoirs in visceral lymphoid tissues of SIV-infected macaques", Mucosal Immunology, Jan. 2020, vol. 13(1), pp. 149-160 (12 pp.), doi: 10.1038/s41385-019-0221-x.
Srona Sengupta et al., "Targeting the Latent Reservoir for HIV-1", HHS Public Access Author manuscript, Immunity, May 15, 2018, vol. 48(5), pp. 1-45 (45 pp.), doi: 10.1016/j.immuni.2018.04.030.
Amina Ait-Ammar et al., "Current Status of Latency Reversing Agents Facing the Heterogeneity of HIV-1 Cellular and Tissue Reservoirs", Frontiers in Microbiology, Jan. 24, 2020, vol. 10, Article 3060, pp. 1-23 (23 pp.), doi: 10.3389/fmicb.2019.03060.

(Continued)

*Primary Examiner* — Jeffrey S Parkin
(74) *Attorney, Agent, or Firm* — Maier & Maier, PLLC

(57) ABSTRACT

A method for treating acquired immune deficiency syndrome (AIDS) in a subject in need thereof. In particular, the method includes the administration of a combination, a kit-of-parts, a composition or a pharmaceutical composition including an interferon-alpha (IFN-α) blocking agent, a type III interferon blocking agent, an antiretroviral (ART) agent and, optionally, an interferon-beta (IFN-β) blocking agent and/or a latency-reversing agent (LRA).

18 Claims, 9 Drawing Sheets

(56) References Cited

OTHER PUBLICATIONS

Nicolas Noel et al., "Interferon-associated therapies toward HIV control: The back and forth", Cytokine Growth Factor Review, Apr. 2018, vol. 40, (47 pp.), doi: 10.1016/j.cytogfr.2018.03.004.

Krystelle Nganou-Makamdop et al., "Type I IFN signaling blockade by a PASylated antagonist during chronic SIV infection suppresses specific inflammatory pathways but does not alter T cell activation or virus replication", PLoS Pathogens, Aug. 24, 2018, vol. 14(8), Article e1007246, pp. 1-20 (20 pp.) doi: 10.1371/journal.ppat.1007246.

Simon J. Waddell et al., "Dissecting interferon-induced transcriptional programs in human peripheral blood cells", PLoS One, Mar. 22, 2010, vol. 5(3), Article e9753, (13 pp.), doi: 10.1371/journal.pone.0009753.

Szu-Han Huang et al., "Latent HIV reservoirs exhibit inherent resistance to elimination by CD8+ T cells", The Journal of Clinical Investigation, Feb. 1, 2018, vol. 128(2), pp. 876-889 (14 pp.), doi: 10.1172/JCI97555.

Wang et al. "Morphine Suppresses IFN Signaling Pathway and Enhances AIDS Virus Infection" PLoS One. Feb. 16, 2012. 7(2):e31167. 8 pages.

\* cited by examiner (A)

(B)

(C)

(A)

(B)

METHOD OF INHIBITING HIV-1 VIRAL REBOUND IN A SUBJECT USING INTERFERON INHIBITORS AND ART

FIELD

The present invention relates to a novel method for treating acquired immune deficiency syndrome (AIDS) in a subject in need thereof. In particular, said method comprises the administration of a combination, a kit-of-parts, a composition or a pharmaceutical composition comprising an interferon-alpha (IFN-α) blocking agent, a type III interferon blocking agent, an antiretroviral (ART) agent and, optionally, an interferon-beta (IFN-β) blocking agent and/or a latency-reversing agent (LRA).

BACKGROUND

Antiretroviral therapy (ART) is thus far, a very efficient therapy in the treatment of patients infected with human immunodeficiency viruses (HIV). Indeed, patients treated with ART have a plasma viremia below detectable levels and thus can have normal life expectancy. However, these treatments are very onerous and can lead to uncertain long-term cytotoxicity for HIV patients (Chun et al., "Durable Control of HIV Infection in the Absence of Antiretroviral Therapy: Opportunities and Obstacles" JAMA, 2019 Jul. 2; 322(1): 27-28).

In addition, the most considerable issue with ART is that when patients stopped their treatment and are thus in an analytic treatment interruption (ATI), a rapid rebound of plasma viremia is observed. This phenomenon suggests that not all HIV-infected cells are eliminated by ART and that some infected cells remains in the organism. The scientific community is thus wondering how and where HIV is able to persist in patient during ART. Two different types of cells were identified: latent and productive infected cells. In patients treated with ART, latent cells were identified in many T-cells types (including stem cell memory, central memory, transitional memory, effector memory and naïve CD4 T cells), suggesting that these cells can contribute to viral rebound after ART arrest, but this mechanism still remains poorly understood (Pitman et al., "Barriers and strategies to achieve a cure for HIV" Lancet HIV, 2018 June; 5(6):e317-e328).

Under ART treatment, lymph nodes and gastrointestinal tract have much higher concentration of HIV DNA and RNA per CD4 T cells than other tissues (e.g. blood). Indeed, in lymph nodes, CD8 cytotoxic T cells have less access to B-cell follicles and thus these cells are protected from the treatment, while in the gastrointestinal tract, many Th17 cells expressing CCR5 are present, cells targeted preferentially by the virus, which can explain the high level of HIV DNA and RNA. Macrophages from different tissues can also be infected and thus persist for example in the brain and this population was demonstrated as being the viral source of the viral rebound after ART arrest in a unique model of humanized myeloid-only mice (Honeycutt et al., "HIV persistence in tissue macrophages of humanized myeloid-only mice during antiretroviral therapy" Nat Med, 2017; 23: 638-43).

Furthermore, the study of Rabezanahary et al., found that in the spleen mesenteric and peripheral lymph nodes of SIVmac251-infected rhesus macaques, effector memory and follicular helper T CD4 have the highest frequency of viral DNA and RNA. Interestingly, two weeks after ART arrest, a viral rebound was observed due to a rapid seeding of SIV from visceral lymphoid tissues producing viral RNA, highlighting the importance of these anatomical sites, reservoirs of HIV, in the viral rebound (Rabezanahary et al., "Despite early antiretroviral therapy effector memory and follicular helper CD4 T cells are major reservoirs in visceral lymphoid tissues of SIV-infected macaques" Mucosal Immunology, 2020 13:149-160). Many other clinical strategies were investigated including targeting the viral replication cycle (BM transplantation of patients with hematopoietic stem cells from donors homozygous for CCD5Δ32 or WT CCR5, gene therapy by editing CCR5, latency reversal agents), HIV-specific immune enhancement strategies (T-cell vaccines, bNAbs and CAR T cells) or immune modulation strategies (immune-checkpoint blockers, vedolizumab, IL15 superagonist or sirolimus) (Pitman et al., "Barriers and strategies to achieve a cure for HIV" Lancet HIV, 2018 June; 5(6):e317-e328).

A new strategy consists in targeting the latent cells which escape the ART and can thus create a viral rebound after ART arrest. One hypothesis was that the HIV integrated mostly into heterochromatin-repressed transcriptional regions into these latent cells, but it was surprisingly found that HIV can be latent while integrated in euchromatin-active transcriptional regions, suggesting that the epigenetic silencing occurs via cis- or trans-acting elements. So far, the therapies were focused on epigenetic mechanisms of latency and mostly histone deacetylase inhibitors (HDAC) inhibitors, but no clear reservoir reduction has been demonstrated. T-cell activating agents were also a new wave of therapy using for example protein kinase C (PKC) agonists but despite promising results in vitro, no reduction in the latent reservoir was reported in vivo. One strategy could also be a "shock and kill" strategy wherein the "shock" phase will be to target the immune response towards the reservoir and to reverse latency and then to kill the cells, but this strategy requires to know which antigen will be presented by the re-activated cell. Many others strategies are currently under investigation (Sengupta et al., "Targeting the Latent Reservoir for HIV-1" Immunity, 2018 15; 48(5):872-895 and Ait-Ammar et al., "Current Status of Latency Reversing Agents Facing the Heterogeneity of HIV-1 Cellular and Tissue Reservoirs" Frontiers in Microbiology, 2020 24; 10:3060).

In summary, latent HIV reservoir represents the main obstacle to achieving sustained virologic remission in ART-treated HIV-infected individuals following ART treatment interruption. And the reservoir cell compartment still needs to be better understood in order to improve the cure strategy against HIV infection.

Thus, there is still an important and urgent need for a novel treatment of HIV infection or acquired immune deficiency syndrome (AIDS) which allows sustained or complete virologic remission in ART-treated HIV patients.

It has been shown that antiviral activity of type I and type III interferon inhibits the HIV viral replication in the latently infected cells localized in immune and mucosal epithelial cells respectively.

Based on their discovery of new biological properties of type I and type III interferons, the inventors propose to improve existing therapeutic strategies for treating AIDS caused by HIV.

In particular, the production of type I IFN-α and type III IFN-λ, locally, which is induced by viral replication occurring in the peripheral and mucosal reservoir cells (which contain latent integrated HIV proviruses), is involved in the incomplete virus clearance.

Indeed, the inventors have shown the presence in the serum of post-cART patients of substantial concentrations of these IFN-α and IFN-λ. These antiviral cytokines are locally produced by peripheral and mucosal cells, which are still infected and replicating the virus.

By their antiviral effects, these interferons locally reduce the ongoing viral replication occurring in these reservoir cells. This limits the local propagation of the virus to nearby cells, but at the time maintains the reservoir of infected cells.

The inventors thus propose to block the type I interferon-α, the type III interferon-λ, and optionally type I IFN interferon-β antiviral action in resistant cells containing proviral HIV-1 DNA in the HIV reservoirs, by repeated administration of specific agents blocking the production or of the activity of these cytokines, to reverse proviral latency, while administering ART agents to the patient until total viral clearance.

Indeed, following the blocking of the peripheral and mucosal antiviral interferons, which hinder expression of viral replication in reservoir cells, the HIV-1 proviral DNA present in these reservoir cells may fully replicate viruses. In turn, cART treatment, which controls viral replication, may reduce and progressively eliminate these peripheral and mucosal cellular reservoirs.

The applicant thus provides a novel method for treating AIDS in a subject in need thereof, comprising administering to the subject a combination comprising:

a) an interferon-alpha (IFN-α) blocking agent,
b) a type III interferon blocking agent,
c) optionally, an interferon-beta (IFN-β) blocking agent,
d) an antiretroviral (ART) agent, and
e) optionally, a latency-reversing agent (LRA).

SUMMARY

The present invention relates to a method for treating acquired immune deficiency syndrome (AIDS) in a subject in need thereof, comprising administering to the subject a combination comprising:

a) an interferon-alpha (IFN-α) blocking agent,
b) a type III interferon blocking agent,
c) optionally, an interferon-beta (IFN-β) blocking agent,
d) an antiretroviral (ART) agent, and
e) optionally, a latency-reversing agent (LRA).

In some embodiments, the IFN-α blocking agent is selected from the group consisting of an agent neutralizing circulating IFN-α, an agent blocking IFN-α signaling, an agent depleting IFN-α producing cells, and/or an agent blocking IFN-α production;

- wherein the agent neutralizing circulating IFN-α is selected from the group comprising active anti-IFN-α vaccine including antiferon or passive anti-IFN-α vaccine including anti-IFN-α antibodies or anti-IFN-α hyper-immune serum;
- wherein the blocking agent of IFN-α signaling is selected from the group of anti-type I interferon R1 or R2 antibodies or from IFN-α endogenous regulators including SOSC1 or aryl hydrocarbon receptors;
- wherein the agent depleting IFN-α producing cells is an agent depleting plasmacytoid dendritic cells (pDCs); and wherein the agent blocking IFN-α production is an agent blocking the production of IFN-α by pDCs.

In some embodiments, the type III interferon blocking agent is an anti-IFN-λ neutralizing antibody, or an agent blocking type III interferon signaling such as a neutralizing antibody directed against the IFNLR1 receptor.

In some embodiments, the IFN-β blocking agent is selected from the group consisting of an agent neutralizing circulating IFN-β, wherein the agent neutralizing circulating IFN-β is anti-IFN-β antibodies or anti-IFN-β hyper-immune serum.

In some embodiments, the antiretroviral (ART) agent is selected from the group consisting of Nucleoside reverse transcriptase inhibitors (NRTIs), Non-nucleoside reverse transcriptase inhibitors (NNRTIs), Protease inhibitors (PIs), Integrase inhibitors (INSTIs), Fusion inhibitors (FIs), Chemokine receptor antagonists (CCR5 antagonists) and Entry inhibitors (CD4-directed post-attachment inhibitors).

In some embodiments, the latency-reversing agent (LRA) is selected from the group consisting of PKC agonists, MAPK agonists, CCR5 antagonists, Tat vaccines, SMAC mimetics, inducers of P-TEFb release, activators of Akt pathway, benzotriazole derivatives, epigenetic modifiers and immunomodulatory LRAs.

In some embodiments, the method further comprises assessing the presence of cells containing replication-competent proviral HIV DNA in a blood sample from the subject.

In some embodiments, the IFN-α blocking agent, the type III interferon blocking agent, optionally the interferon-beta (IFN-β) blocking agent, the antiretroviral (ART) agent, and optionally the latency-reversing agent are administered simultaneously, separately or sequentially.

In some embodiments, the IFN-α blocking agent, the type III interferon blocking agent, and optionally the interferon-beta (IFN-β) blocking agent are administered simultaneously.

In some embodiments, the IFN-α blocking agent, the type III interferon blocking agent, and optionally the interferon-beta (IFN-β) blocking agent are administered every week, every 2 weeks or every 3 weeks.

In some embodiments, the antiretroviral (ART) agent, and optionally the latency-reversing agent are administered daily.

In some embodiments, the IFN-α blocking agent, the type III interferon blocking agent, and optionally the interferon-beta (IFN-β) blocking agent are administered parenterally or intravenously.

In some embodiments, the antiretroviral (ART) agent, and optionally the latency-reversing agent are administered orally.

In some embodiments, the subject receives one or more doses of the IFN-α blocking agent, the type III interferon blocking agent, and optionally the interferon-beta (IFN-β) blocking agent before receiving said combination.

In some embodiments, the subject receives one or more doses of the antiretroviral (ART) agent, and optionally the latency-reversing agent, before receiving said combination.

In some embodiments, said combination is administered to the subject until no cell containing replication-competent proviral HIV DNA is detected in a blood sample from the subject.

In some embodiments, the subject is infected with a human immunodeficiency virus (HIV) strain, preferably an HIV-1 strain or an HIV-2 strain.

In some embodiments, said method is for curatively treating acquired immune deficiency syndrome (AIDS) in a subject in need thereof.

In some embodiments, said method is for prophylactically treating acquired immune deficiency syndrome (AIDS) in a subject in need thereof.

Another aspect of the invention relates to a kit-of-parts or a combination comprising:

a) an interferon-alpha (IFN-α) blocking agent,
b) a type III interferon blocking agent, c) optionally, an interferon-beta (IFN-β) blocking agent,
d) an antiretroviral (ART) agent, and
e) optionally, a latency-reversing agent (LRA).

DETAILED DESCRIPTION

Figure 1:
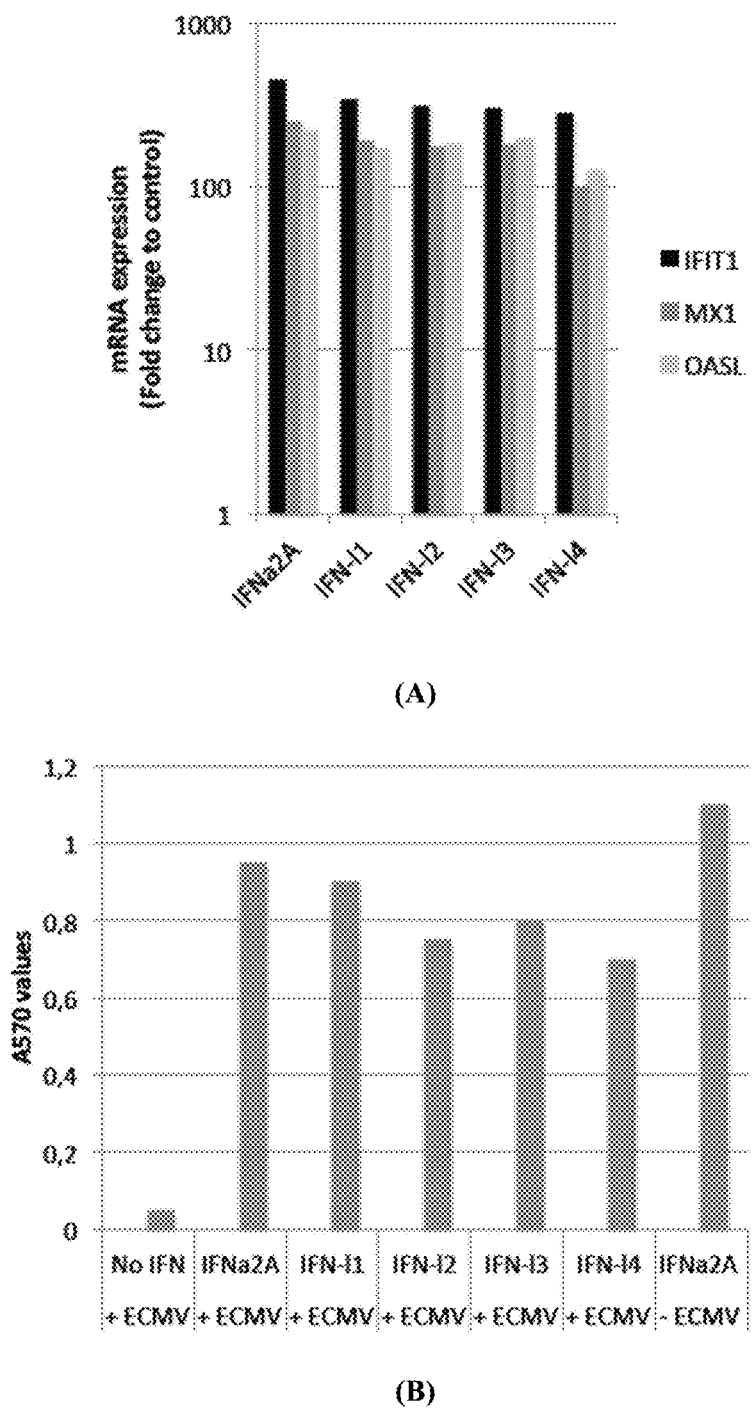
FIG. 1. Antiviral activity of type I and type III interferons. (A) Expression of ISGs in HepG2. HepG2 cells were treated with IFNα2a or IFNλ1-4 (10 ng/ml). After 4 h of stimulation, qRT-PCR were used to examine the mRNA levels of the interferon-induced genes, IFIT1, MX1 and OASL and fold-changes was calculated by $2^{-\Delta\Delta Ct}$ method as compared with non-treated cell control and using endogenous S14 mRNA level for normalization. (B) Antiviral activity of type I and III IFNs against EMCV. IFNα2a or IFNλ1/2/3/4 (10 ng/ml) were added to HepG2 cells 24 h prior to challenge with EMCV. Forty-eight after infection with EMCV, cells were assayed for viability with a bioassay. A570 values were directly proportional to cell viability and therefore antiviral activity of the respective IFNs. IFN-α treatment without viral challenge was used as a baseline of the viability of the cells.

In the present invention, the following terms have the following meanings:

"About" preceding a figure encompasses plus or minus 10%, or less, of the value of said figure. It is to be understood that the value to which the term "about" refers is itself also specifically, and preferably, disclosed.

As used herein, the term "adjuvant" refers to a compound or combination of compounds that helps and enhances the pharmacological effect of a drug or a vaccine, or increases an immunogenic response.

The term "administering" means either directly administering a compound or composition of the present invention, or administering a prodrug, derivative or analog which will form an equivalent amount of the active compound or substance within the body. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

The term "antigen" refers to a compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance.

The term "decrease" refers to reducing the quality, amount, or strength of something. For example, a therapy (such as the methods provided herein) decreases the infectious load or titer of a pathogen such as HIV, or one or more symptoms associated with infection.

The term "fragment" refers to a portion of a polypeptide that exhibits at least one useful epitope. The phrase "functional fragment(s) of a polypeptide" refers to all fragments of a polypeptide that retain an activity, or a measurable portion of an activity, of the polypeptide from which the fragment is derived. Fragments, for example, can vary in size from a polypeptide fragment as small as an epitope capable of binding an antibody molecule to a large polypeptide capable of participating in the characteristic induction or programming of phenotypic changes within a cell. An epitope is a region of a polypeptide capable of binding an immunoglobulin generated in response to contact with an antigen.

The term "immunogenic peptide" (or "antigenic peptide") refers to a peptide which comprises an allele-specific motif or other sequence, such as an N-terminal repeat, such that the peptide will bind an MHC molecule and induce a cytotoxic T lymphocyte ("CTL") response, or a B cell response (for example antibody production) against the antigen from which the immunogenic peptide is derived. In one embodiment, immunogenic peptides are identified using sequence motifs or other methods, such as neural net or polynomial determinations known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide.

The term "immunity" refers to the state of being able to mount a protective response upon exposure to an immunogenic agent. Protective responses can be antibody-mediated or immune cell-mediated, and can be directed toward a particular pathogen or tumor antigen Immunity can be acquired actively (such as by exposure to an immunogenic agent, either naturally or in a pharmaceutical composition) or passively (such as by administration of antibodies or in vitro stimulated and expanded T cells).

As used herein, the term "alpha interferon" (IFN-α) or "interferon-alpha" refers to a family of more than 20 related but distinct members encoded by a cluster on chromosome 9 and all bind to the same IFN receptor. Among these, the IFN-α2 have 3 recombinant variants (α2a, α2b, α2c) depending upon the cells of origin and the IFN-α2b is the predominant variant in human genome. There is evidence though that each subtype has a different binding capacity to the IFNAR, modulating the signaling transduction events and the biological effects in the target cells.

The term "type III interferon", also called interferon-lambda (IFN-λ) refers to naturally occurring and/or recombinant cytokines of the type III interferon-lambda family There are four IFN-λ members in humans, IFN-λ1/IL-29, IFN-λ2/IL-28A, IFN-λ3/IL-λ4, The term "beta interferon" (IFN-β) or "interferon-beta" refers to a family of two related but distinct members IFN-β1 and IFN-β3. They both bind to the same IFN receptor, the IFN-α receptor (IFNAR), which is a cell surface receptor complex consisting of 2 chains: IFNAR1 and IFNAR2 (IFNAR1/IFNAR2 heterodimer). Binding of IFN-β to the IFNAR receptor triggers signaling transduction events and biological effects in the target cell.

The term "isolated" or "non-naturally occurring" with reference to a biological component (such as a nucleic acid molecule, protein organelle or cells), refers to a biological component altered or removed from the natural state. For example, a nucleic acid or a peptide naturally present in a living animal is not "isolated," but the same nucleic acid or peptide partially or completely separated from the coexisting materials of its natural state is "isolated". An isolated nucleic acid or peptide can exist in substantially purified form, or can exist in a non-native environment such as, for example, a host cell. Typically, a preparation of isolated nucleic acid or peptide contains the nucleic acid or peptide at least about 80% pure, at least about 85% pure, at least about 90% pure, at least about 95% pure, greater than 95% pure, greater than about 96% pure, greater than about 97% pure, greater than about 98% pure, or greater than about 99% pure. Nucleic acids and proteins that are "non-naturally occurring" or have been "isolated" include nucleic acids and proteins purified by standard purification methods. The term also embraces nucleic acids and proteins prepared by recombinant expression in a host cell as well as chemically synthesized nucleic acids. An "isolated polypeptide" is one that has been identified and separated and/or recovered from a component of its natural environment.

The terms "subject", "individual," and "patient" are used interchangeably herein, and refer to an animal, for example a mammal, primate or human, and include all mammals, such as e.g. non-human primate, (particularly higher primates), sheep, dog, rodent, (e.g. mouse or rat), guinea pig, goat, pig, cat, rabbits, cows, horses. In particular, these terms refer to a human, to whom treatment, including prophylactic treatment, with the combination according to the present invention, is provided.

The term "mutation" refers to any difference in a nucleic acid or polypeptide sequence from a normal, consensus or "wild type" sequence. A mutant is any protein or nucleic acid sequence comprising a mutation. In addition, a cell or an organism with a mutation may also be referred to as a mutant. Some types of coding sequence mutations include point mutations (differences in individual nucleotides or amino acids); silent mutations (differences in nucleotides that do not result in an amino acid changes); deletions (differences in which one or more nucleotides or amino acids are missing, up to and including a deletion of the entire coding sequence of a gene); frameshift mutations (differences in which deletion of a number of nucleotides indivisible by 3 results in an alteration of the amino acid sequence. A mutation that results in a difference in an amino acid may also be called an amino acid substitution mutation. Amino acid substitution mutations may be described by the amino acid change relative to wild type at a particular position in the amino acid sequence.

As used herein, the terms "prevent", "preventing" and "prevention" refer to preventative measures, wherein the object is to reduce the chances that a subject will develop the pathologic condition or disorder over a given period of time. Such a reduction may be reflected, e.g., in a delayed onset of at least one symptom of the pathologic condition or disorder in the subject.

The term "prophylactic" refers to a treatment administered to a subject who does not exhibit signs of a disease or exhibits only early signs for the purpose of decreasing the risk of developing pathology. In particular, a prophylactic treatment of a HIV or SIV infection in a subject refers to a treatment that allows the subject to become an elite controller (EC) i.e. to have a relatively high CD4+ T cell count (such as e.g. superior to 500 CD4+ T cells per microliter) and/or to maintain clinically undetectable plasma HIV-1 RNA level (such as e.g. HIV RNA<50 copies/mL) during a prolonged period of time in the absence of any antiretroviral treatment (ART).

The term "therapeutic" refers to a treatment administered to a subject who exhibit early or established signs of a disease.

The term "curative" refers to a treatment administered to a subject suffering from a disease for the purpose of curing the disease, i.e. of making any sign of the disease disappear or becoming undetectable.

The terms "protein", "peptide", "polypeptide", and "amino acid sequence" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "sample" or "biological sample" refers to a biological specimen obtained from a subject, such as a cell, fluid of tissue sample. In some cases, biological samples contain genomic DNA, RNA (including mRNA and microRNA), protein, or combinations thereof. Examples of samples include, but are not limited to, saliva, blood, serum, urine, spinal fluid, tissue biopsy, surgical specimen, cells (such as PBMCs, white blood cells, lymphocytes, or other cells of the immune system) and autopsy material.

As used herein, the term "treatment" refers to an intervention that ameliorates a sign or symptom of a disease or pathological condition. For example, in case of HIV infection, HIV RNA (viral load) and CD4 T lymphocyte (CD4) cell count are the two surrogate markers of antiretroviral treatment (ART) responses and HIV disease progression that have been used for decades to manage and monitor HIV infection. Thus, the efficacy of the treatment may be evaluated by the plasma viral RNA load of a "treated" human before and after the treatment, if it is reduced by at least about 10%, 20%, 30%, 40%, 50%, more preferably by at least about 70%, yet more preferably by at least about 75% or 80% or 85% or 90% or 95% or 98% or 99%, or even more (99.5%, 99.8%, 99.9%, 100%) the treatment is considered as effective, and/or by the monitoring of CD4 cell count before and after the treatment, if the absolute count of CD4 cell is increased by at least about 5%, 10%, 15%, 20%, 25%, more preferably by at least about 30%, yet more preferably by at least about 35% or 40% or 45% or 50% or 55% or 60% or 65%, or even more the treatment is considered as effective. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A therapeutic treatment is a treatment administered to a subject after signs and symptoms of the disease have developed. A prophylactic treatment is a treatment administered to a subject who does not exhibit signs of a disease or exhibits only early signs, for the purpose of decreasing the risk of developing pathology. Also, a prophylactic treatment of a HIV or SIV infection in a subject refers to a treatment that allows the subject to become an elite controller (EC) i.e. to have a relatively high CD4+ T cell count (such as e.g. superior to 500 CD4+ T cells per microliter) and/or to maintain clinically undetectable plasma HIV-1 RNA level (such as e.g. HIV RNA<50 copies/mL) during a prolonged period of time in the absence of any antiretroviral treatment (ART). A prophylactic treatment is a treatment administered to a subject suffering from a disease for the purpose of curing the disease, i.e. of making any sign of the disease disappear or becoming undetectable.

As used herein, the term "vaccine" refers to an immunogenic product or composition that can be administered to a mammal, such as a human, to confer immunity, such as passive or active immunity, to a disease or other pathological condition. Vaccines can be used preventively or therapeutically, either prophylactically or curatively. Thus, vaccines can be used to reduce the likelihood of developing a disease (such as infection) or to reduce the severity of symptoms of a disease or condition, limit the progression of the disease or condition (such as infection), or limit the recurrence of a disease or condition.

The term "virus" refers to microscopic infectious organism that reproduces inside living cells. A virus consists essentially of a core of nucleic acid (the viral genome) surrounded by a protein coat (capsid), and has the ability to replicate only inside a living cell. "Viral replication" is the production of additional virus particles by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so. Particular viral species can alternatively enter into a "lysogenic" or "latent" infection. In the establishment of latency, the viral genome is replicated, but capsid proteins are not produced and assembled into viral particles.

The invention relates to a method for treating acquired immune deficiency syndrome (AIDS) in a subject in need thereof, comprising administering to the subject a combination comprising:

a) an interferon-alpha (IFN-α) blocking agent,
b) a type III interferon blocking agent,
c) optionally, an interferon-beta (IFN-β) blocking agent,
d) an antiretroviral (ART) agent, and
e) optionally, a latency-reversing agent (LRA).

In one embodiment, the method comprises administering to the subject a) an interferon-alpha (IFN-α) blocking agent, b) a type III interferon blocking agent, and d) an antiretroviral (ART) agent.

In another embodiment, the method comprises administering to the subject a) an interferon-alpha (IFN-α) blocking agent, b) a type III interferon blocking agent, c) an interferon-beta (IFN-β) blocking agent, and d) an antiretroviral (ART) agent.

In another embodiment, the method comprises administering to the subject a) an interferon-alpha (IFN-α) blocking agent, b) a type III interferon blocking agent, c) an interferon-beta (IFN-β) blocking agent, d) an antiretroviral (ART) agent, and e) optionally, a latency-reversing agent (LRA).

In some embodiments, the method is a method of prophylactic treatment.

In some embodiments, the method is a method of curative treatment.

The present invention further relates to a combination comprising:
   a) an interferon-alpha (IFN-α) blocking agent,
   b) a type III interferon blocking agent,
   c) optionally, an interferon-beta (IFN-β) blocking agent,
   d) an antiretroviral (ART) agent, and
   e) optionally, a latency-reversing agent (LRA).

The present invention also relates to a combination for use as a medicament, wherein said combination comprises:
   a) an interferon-alpha (IFN-α) blocking agent,
   b) a type III interferon blocking agent,
   c) optionally, an interferon-beta (IFN-β) blocking agent,
   d) an antiretroviral (ART) agent, and
   e) optionally, a latency-reversing agent (LRA).

The present invention also relates to a combination for use in the treatment of acquired immune deficiency syndrome (AIDS) in a subject in need thereof, wherein said combination comprises:
   a) an interferon-alpha (IFN-α) blocking agent,
   b) a type III interferon blocking agent,
   c) optionally, an interferon-beta (IFN-β) blocking agent,
   d) an antiretroviral (ART) agent, and
   e) optionally, a latency-reversing agent (LRA).

In one embodiment, the combination for use comprises a) an interferon-alpha (IFN-α) blocking agent, b) a type III interferon blocking agent, and d) an antiretroviral (ART) agent.

In one embodiment, the combination for use comprises a) an interferon-alpha (IFN-α) blocking agent, b) a type III interferon blocking agent, c) an interferon-beta (IFN-β) blocking agent, and d) an antiretroviral (ART) agent.

In one embodiment, the combination for use comprises a) an interferon-alpha (IFN-α) blocking agent, b) a type III interferon blocking agent, c) an interferon-beta (IFN-β) blocking agent, d) an antiretroviral (ART) agent, and e) optionally, a latency-reversing agent (LRA).

The present invention further relates to a kit-of-parts comprising:
   a) an interferon-alpha (IFN-α) blocking agent,
   b) a type III interferon blocking agent,
   c) optionally, an interferon-beta (IFN-β) blocking agent,
   d) an antiretroviral (ART) agent, and
   e) optionally, a latency-reversing agent (LRA).

The present invention further relates to a kit-of-parts for use as a medicament, wherein said kit-of-parts comprises:
   a) an interferon-alpha (IFN-α) blocking agent,
   b) a type III interferon blocking agent,
   c) optionally, an interferon-beta (IFN-β) blocking agent,
   d) an antiretroviral (ART) agent, and
   e) optionally, a latency-reversing agent (LRA).

The present invention also relates to a kit-of-parts for use in the treatment of acquired immune deficiency syndrome (AIDS) in a subject in need thereof, wherein said kit-of-parts comprises:
   a) an interferon-alpha (IFN-α) blocking agent,
   b) a type III interferon blocking agent,
   c) optionally, an interferon-beta (IFN-β) blocking agent,
   d) an antiretroviral (ART) agent, and
   e) optionally, a latency-reversing agent (LRA).

In one embodiment, the kit-of-parts for use comprises a) an interferon-alpha (IFN-α) blocking agent, b) a type III interferon blocking agent, and d) an antiretroviral (ART) agent.

In one embodiment, the kit-of-parts for use comprises a) an interferon-alpha (IFN-α) blocking agent, b) a type III interferon blocking agent, c) an interferon-beta (IFN-β) blocking agent, and d) an antiretroviral (ART) agent.

In one embodiment, the kit-of-parts for use comprises a) an interferon-alpha (IFN-α) blocking agent, b) a type III interferon blocking agent, c) an interferon-beta (IFN-β) blocking agent, d) an antiretroviral (ART) agent, and e) optionally, a latency-reversing agent (LRA).

According to the present invention, the combination or kit-of-parts as described herein is for use in the treatment of acquired immune deficiency syndrome (AIDS) in a subject in need thereof.

In one embodiment, the subject is infected with a human immunodeficiency virus (HIV), or a simian immunodeficiency virus (SIV).

Thus, the combination or kit-of-parts as described herein is also for use in the treatment of a human immunodeficiency virus (HIV) infection or a simian immunodeficiency virus (SIV) infection.

Due to the great variability in the HIV genome, which results from mutation, recombination, insertion and/or deletion, HIV has been classified in groups, subgroups, types, subtypes and genotypes. There are two major HIV groups (HIV-1 and HIV-2) and many subgroups because the HIV genome mutates constantly. The major difference between the groups and subgroups is associated with the viral envelope. HIV-1 is classified into a main group (M), said group M being divided into least nine genetically distinct subtypes. These are subtypes A, B, C, D, F, G, H, J and K. Many other subtypes resulting from in vivo recombination of the previous ones also exist (e.g., CRF). In one embodiment, the HIV antigen is related to a specific HIV group, subgroup, type, subtype or to a combination of several subtypes.

In one embodiment, the HIV virus is HIV-1 or HIV-2, preferably HIV-1.

In one embodiment, the subject is infected with an HIV-1 strain or an HIV-2 strain.

Thus, the combination or kit-of-parts as described herein is also for use in the treatment of an HIV-1 strain or an HIV-2 strain.

In one embodiment, the HIV-1 virus is from group M and preferably subtype B (HXB2).

In one embodiment, the subject is a mammal, a primate, preferably a human.

In an embodiment, the combination or kit-of-parts as described herein is for use in the prophylactic treatment of acquired immune deficiency syndrome (AIDS) in a subject in need thereof.

In another embodiment, the combination or kit-of-parts as described herein is for use in the curative treatment of acquired immune deficiency syndrome (AIDS) in a subject in need thereof.

As used herein, the term "alpha interferon" (IFN-α) or "interferon-alpha" refers to a family of more than 20 related but distinct members encoded by a cluster on chromosome 9 and all bind to the same IFN receptor. Among these, the IFN-α2 have 3 recombinant variants (α2a, α2b, α2c)

depending upon the cells of origin and the IFN-α2b is the predominant variant in human genome. There is evidence though that each subtype has a different binding capacity to the IFNAR, modulating the signaling transduction events and the biological effects in the target cells.

In one embodiment, the interferon-alpha blocking agent described herein is an agent neutralizing circulating IFN-α and/or an agent blocking IFN-α signaling, and/or an agent depleting IFN-α producing cells, and/or an agent blocking IFN-α production.

In one embodiment, the interferon-alpha blocking agent described herein comprises at least one agent selected from: an agent neutralizing circulating IFN-α and/or an agent blocking IFN-α signaling, and/or an agent depleting IFN-α producing cells, and/or an agent blocking IFN-α production.

In one embodiment, the agent neutralizing circulating IFN-α and/or the agent blocking IFN-α signaling, and/or the agent depleting IFN-α producing cells, and/or the agent blocking IFN-α production is/are an IFN-α antagonist.

In some embodiments, wherein the interferon-alpha blocking agent is selected from the group consisting of: an agent neutralizing circulating alpha interferon, an agent blocking interferon-alpha signaling, an agent depleting IFN-α producing cells, and/or an agent blocking IFN-α production, wherein the agent neutralizing circulating alpha interferon is selected from the group comprising active anti-IFN-α vaccine including antiferon or passive anti-IFN-α vaccine including anti-IFN-α antibodies or anti-IFN-α hyper-immune serum, wherein the blocking agent of interferon-alpha signaling is selected from the group of anti-type I interferon R1 or R2 antibodies or from interferon-alpha endogenous regulators including SOSC1 or aryl hydrocarbon receptors, wherein the agent depleting IFN-α producing cells is an agent depleting plasmacytoid dendritic cells (pDCs), and wherein the agent blocking IFN-α production is an agent blocking the production of IFN-α by pDCs.

In some embodiments, the interferon-alpha blocking agent is an agent neutralizing circulating alpha interferon selected from the group consisting of active anti-IFN-α vaccine including antiferon or passive anti-IFN-α vaccine including anti-IFN-α antibodies or anti-IFN-α hyper-immune serum, and wherein the blocking agent of interferon-alpha signaling is selected from the group consisting of anti-type I interferon R1 or R2 antibodies, SOSC1 and aryl hydrocarbon receptors.

As used herein, the term "alpha interferon antagonist" refers to a substance which interferes with or inhibits the IFN-α biological activity. "IFN-α biological activity" as used herein refers to any activity occurring as a result of IFN-α binding to its receptor IFNAR (IFNAR1/IFNAR2 heterodimer). Such binding can, for example, activate the JAK-STAT signaling cascade, and trigger tyrosine phosphorylation of a number of proteins including JAKs, TYK2, STAT proteins. Thus, the signaling blocking agent of interferon can neutralize the fixation of the INF-α to its receptor and/or block the signaling cascade induced by the binding of IFN-α to its receptor. In some embodiments, the IFN-α antagonist is selected from the group of active anti-IFN-α vaccine (e.g., antiferon) or passive anti-IFN-α vaccine (e.g., anti-IFN-α antibody or anti-IFN-α hyper-immune serum). See for example Noel et al. (2018). Cytokine Growth Factor Rev 40:99-112.

In one embodiment, the agent neutralizing circulating IFN-α described herein is an IFN-α ligand inhibitor.

In one embodiment, the agent neutralizing circulating IFN-α is an anti-IFN-α antibody, preferably a neutralizing antibody. The anti-IFN-α antibody may be a monoclonal or a polyclonal antibody.

Examples of anti-IFN-α antibodies include, without limitation, Sifalimumab, Rontalizumab, MMHA-1 clone, MMHA-2 clone, MMHA-6 clone, MMHA-8 clone, MMHA-9 clone, MMHA-11 clone, MMHA-13 clone and MMHA-17 clone.

In one embodiment, the agent neutralizing circulating IFN-α is an anti-IFN-α hyper-immune serum.

In one embodiment, the agent neutralizing circulating IFN-α described herein is an antiferon, such as, for example, an IFN-α-Kinoid.

In one embodiment, the agent neutralizing circulating IFN-α is a soluble receptor that binds IFN-α.

In one embodiment, the agent blocking IFN-α signaling described herein is an IFNAR antagonist.

In one embodiment, the agent blocking IFN-α signaling is an IFNAR1 antagonist. In another embodiment, the agent blocking IFN-α signaling is an IFNAR2 antagonist.

In one embodiment, the agent blocking IFN-α signaling is an antibody that binds to IFNAR1 or IFNAR2.

In one embodiment, the agent blocking IFN-α signaling is an agent that antagonizes the type I IFN signaling pathway.

In one embodiment, the agent blocking IFN-α signaling can be an inhibitor of type I IFN signaling pathway. Type I IFN signaling pathway inhibitors are well known in the art and include, without limitation, JAK1/2/3 inhibitors and STAT inhibitors. Accordingly, in one embodiment, the agent blocking IFN-α signaling is selected from JAK1/2/3 inhibitors, STAT inhibitors, and Tyrosine Kinase 2 (TYK2) inhibitors. Non-limiting examples of JAK1/2/3 inhibitors include Ruxolitinib, Tofacitinib and Baricitinib. Non-limiting examples of TYK2 inhibitors include the BMS-986165 inhibitor.

In one embodiment, the agent blocking IFN-α signaling can be an endogenous negative regulator of type I IFN signaling pathway. Endogenous negative regulators are well known in the art and include, without limitation, SOCS1/3, FOXO3, Aryl hydrocarbon Receptor (AhR) or other negative regulators. Accordingly, in one embodiment, the agent blocking interferon signaling is selected from SOCS1/3, FOXO3 or Aryl hydrocarbon Receptor (AhR).

In one embodiment, the agent blocking IFN-α signaling is a PASylated antagonist. PASylated antagonist of type I IFN are known in the art, see for example Nganou-Makamdop et al. (2018). PLoS Pathog 14(8): e1007246.

In one embodiment, the IFN-α antagonist described herein is an agent depleting IFN-α producing cells.

As used herein, the term "IFN-α producing cells" refers to any cell that produce IFN-α. In particular, it is well known in the art that the plasmacytoid dendritic cells (pDCs) are the main producer of IFN-α. Thus, in one embodiment, the agent depleting IFN-α producing cells depletes pDCs.

In one embodiment, the agent depleting IFN-α producing cells is an antibody. In one embodiment, the antibody depletes pDCs, such as, for example, an anti-CD123 antibody (i.e., anti-IL-3RA).

In one embodiment, the IFN-α antagonist described herein is an agent that blocks the production of IFN-α.

In one embodiment, the agent that blocks the production of the IFN-α is an antibody. In one embodiment, the antibody blocks the production of IFN-α by pDCs. Said antibody can be, for example, an anti-BDCA2 (Blood DC Antigen 2) antibody.

In some embodiments, the interferon-alpha blocking agent selected from the group consisting of:
- an anti-IFN-α antibody, preferably Sifalimumab, Rontalizumab, MMHA-1 clone, MMHA-2 clone, MMHA-6 clone, MMHA-8 clone, MMHA-9 clone, MMHA-11 clone, MMHA-13 clone or MMHA-17 clone,
- an anti-IFN-α hyper-immune serum,
- an antiferon, preferably an IFN-α-Kinoid,
- a soluble receptor that binds IFN-α,
- an IFNAR1 or IFNAR2 antagonist, preferably an antibody that binds to IFNAR1 or IFNAR2,
- a type I IFN signaling pathway inhibitors selected from a STAT inhibitor, a JAK1/2/3 inhibitor, such as e.g. Ruxolitinib, Tofacitinib or Baricitinib, and a TYK2 inhibitor, such as e.g. BMS-986165,
- an endogenous negative regulator of type I IFN signaling pathway selected from SOCS1/3, FOXO3, Aryl hydrocarbon Receptor (AhR) or another negative regulator,
- a PASylated antagonist, an antibody depleting pDCs, preferably an anti-CD123 (i.e. anti-IL-3RA) antibody,
- an antibody blocking the production of IFN-α by pDCs, preferably an anti-BDCA2 (Blood DC Antigen 2) antibody.

In one embodiment, the interferon-alpha blocking agent is an anti-IFN-α antibody, preferably a monoclonal antibody, more preferably a neutralizing antibody.

As used herein, the term "type III interferon", also called interferon-lambda (IFN-λ), refers to naturally occurring and/or recombinant cytokines of the type III interferon-lambda family There are four IFN-λ members in humans, IFN-λ1/IL-29, IFN-λ2/IL-28A, IFN-λ3/IL-28B, IFN-λ4.

In one embodiment, the type III interferon is IFN-λ.

In one embodiment, the IFN-λ refers to at least one IFN-λ subtype, i.e. IFN-λ1, IFN-λ2 IFN-λ3, IFN-λ4.

In one embodiment, the human IFN-λ1 has the following accession number NP_742152.1. In one embodiment, the human IFN-λ2 has the following accession number NP_742150.1. In one embodiment, the human IFN-λ3 has the following accession numbers NP_001333866.1 (isoform 1) or NP_742151.2 (isoform 2). In one embodiment, the human IFN-λ4 has the following accession number NP_001263183.2.

In one embodiment, the interferon-lambda blocking agent is an anti-IFN-λ antibody, preferably a monoclonal antibody, more preferably a neutralizing antibody. The anti-interferon-lambda antibody may be a monoclonal or a polyclonal antibody.

Non limiting examples of neutralizing anti-interferon-lambda antibodies include:
- the monoclonal anti-IL-29 (IFN-λ1) antibody clone 6A11 (Invivogen),
- the monoclonal anti-human IL-29 (IFN-λ1) antibody clone #247801 (R&D systems),
- the monoclonal anti-IL-28A (IFN-λ2) antibody clone 21C3 (Invivogen),
- the monoclonal anti-IL-28 A (IFN-λ2) antibody clone MMHL-2 (PBL assay sciences),
- the monoclonal anti-human IL-28A (IFN-λ2) antibody Clone #248526 (R&D systems),
- the polyclonal anti-human IL-28A (IFN-λ2) antibody (R&D systems),
- the monoclonal anti IL-28 B (IFN-λ3) antibody clone 18F4 (Invivogen), and
- the monoclonal anti-IL-28 B (IFN-λ3) antibody clone MMHL-3 (PBL assay sciences).

In another embodiment, the type III interferon blocking agent is an agent blocking type III interferon signaling.

In one embodiment, the agent blocking type III interferon signaling is an antibody.

Such antibody can block or inhibit the biological effects of interferon-lambda and/or block or inhibit the type III interferon signaling pathway. For example, such antibody may bind to an epitope on the interferon-lambda receptor, impeding the binding of interferon-lambda to its receptor and thus the receptor signaling subsequent activation. The heterodimeric receptor complex of interferon-lambda (IFNLR) comprises IFNLR1 (IFNLRA, IL-28RA), and IL10R2 (IL-10RB). IFNLR1 confers ligand specificity and enables receptor assembly, while IL10R2 is shared with IL-10 family members and is required for signaling.

Thus, in one embodiment, the agent blocking type III interferon signaling is an antibody directed against the IFNLR1 receptor.

Non-limiting examples of antibodies directed against the IFNLR1 receptor include the clone MMHLR-1 (Pill assay sciences) and the MHLICR2A1 antibody (Creative Biolabs).

In another embodiment, the interferon-lambda blocking agent is a small chemical molecule entity (such as, for example, a chemical entity with a molecular weight less than 900 Daltons). Methods of screening chemical libraries to identify small chemical molecule entities which may be potential drug candidates are known in the art. For example, a chemical library may be tested in a ligand-receptor binding assay. For instance, the small chemical molecule may bind and block the IFNLR1 receptor.

In another embodiment, the agent blocking type III interferon signaling is selected from JAK1/2/3 inhibitors, STAT inhibitors, and Tyrosine Kinase 2 (TYK2) inhibitors. Non-limiting examples of JAK1/2/3 inhibitors include Ruxolitinib, Tofacitinib and Baricitinib. Non-limiting examples of TYK2 inhibitors include the BMS-986165 inhibitor.

As used herein, the term "beta interferon" (IFN-β) or "interferon-beta" refers to a family of two related but distinct members IFN-β1 and IFN-β3. They both bind to the same IFN receptor, the IFN-α receptor (IFNAR), which is a cell surface receptor complex consisting of 2 chains: IFNAR1 and IFNAR2 (IFNAR1/IFNAR2 heterodimer).

Binding of IFN-β to the IFNAR receptor triggers signaling transduction events and biological effects in the target cell.

In one embodiment, the interferon-beta blocking agent described herein is an agent neutralizing circulating IFN-β and/or an agent blocking IFN-β signaling.

In one embodiment, the interferon-beta blocking agent described herein comprises at least one agent selected from an agent neutralizing circulating IFN-β and an agent blocking IFN-β signaling.

In one embodiment, the agent neutralizing circulating IFN-β and/or the agent blocking IFN-β signaling is/are an IFN-β antagonist.

As used herein, the term "beta interferon antagonist" refers to a substance which interferes with or inhibits the IFN-β biological activity. "IFN-β biological activity" as used herein refers to any activity occurring as a result of IFN-β binding to its receptor IFNAR (IFNAR1/IFNAR2 heterodimer). Such binding can, for example, activate the JAK-STAT signaling cascade, and trigger tyrosine phosphorylation of a number of proteins including JAKs, TYK2, STAT proteins. Thus, the signaling blocking agent of interferon can neutralize the fixation of the IFN-β to its receptor and/or block the signaling cascade induced by the binding of IFN-β to its receptor. In some embodiments, the IFN-β antagonist is selected from the group of anti-IFN-β antibody, anti-IFN-β hyper-immune serum.

In one embodiment, the interferon-beta blocking agent is an agent neutralizing circulating IFN-β, wherein the agent neutralizing circulating IFN-β is an anti-IFN-β antibody or anti-IFN-β hyper-immune serum.

In one embodiment, the agent neutralizing circulating IFN-β is an anti-IFN-β antibody, preferably a neutralizing antibody. The anti-IFN-β antibody may be a monoclonal or a polyclonal antibody.

Non-limiting examples of anti-IFN-β antibodies include:
the neutralizing monoclonal antibody against human IFN-beta, clone 10B10 (Invivogen)
the polyclonal anti-human IFN-beta antibodies (R&D systems)
the monoclonal anti-human IFN-beta antibodies clone #76703, clone #MMHB-3 and clone #937912 (R&D systems)
the neutralizing polyclonal anti-human IFN-beta goat IgG (PBL assay sciences).

In one embodiment, the agent neutralizing circulating IFN-β is an anti-IFN-β hyper-immune serum.

In one embodiment, the agent neutralizing circulating IFN-β described herein is an IFN-β ligand inhibitor.

In one embodiment, the agent neutralizing circulating IFN-β is a soluble receptor that binds IFN-β.

In one embodiment, the interferon-beta blocking agent is an agent blocking IFN-β signaling, wherein the blocking agent of IFN-β signaling is selected from the group consisting of anti-type I interferon R1 or R2 antibodies, SOSC1 and aryl hydrocarbon receptors.

In one embodiment, the agent blocking IFN-β signaling described herein is an IFNAR antagonist. In one embodiment, the agent blocking IFN-β signaling is an IFNAR1 antagonist. In another embodiment, the agent blocking IFN-β signaling is an IFNAR2 antagonist.

In one embodiment, the agent blocking IFN-β signaling is an antibody that binds to IFNAR1 or IFNAR2.

In one embodiment, the agent blocking IFN-β signaling is an agent that antagonizes the type I IFN signaling pathway.

In one embodiment, the agent blocking IFN-β signaling can be an inhibitor of type I IFN signaling pathway. Type I IFN signaling pathway inhibitors are well known in the art and include, without limitation, JAK1/2/3 inhibitors and STAT inhibitors. Accordingly, in one embodiment, the agent blocking IFN-β signaling is selected from JAK1/2/3 inhibitors, STAT inhibitors, and Tyrosine Kinase 2 (TYK2) inhibitors. Non-limiting examples of JAK1/2/3 inhibitors include Ruxolitinib, Tofacitinib and Baricitinib. Non-limiting examples of TYK2 inhibitors include the BMS-986165 inhibitor.

In one embodiment, the agent blocking IFN-β signaling can be an endogenous negative regulator of type I IFN signaling pathway. Endogenous negative regulators are well known in the art and include, without limitation, SOCS1/3, FOXO3, Aryl hydrocarbon Receptor (AhR) or other negative regulators. Accordingly, in one embodiment, the agent blocking interferon signaling is selected from SOCS1/3, FOXO3 or Aryl hydrocarbon Receptor (AhR).

In one embodiment, the agent blocking IFN-β signaling is a PASylated antagonist. PASylated antagonist of type I IFN are known in the art, see for example Nganou-Makamdop et al. (2018). PLoS Pathog 14(8): e1007246.

As used herein, the term "antiretroviral therapy" or "ART" or "highly active antiretroviral therapy" or "HAART" refers to any combination of antiretroviral (ARV) drugs to maximally suppress the HIV virus (e.g., reduce viral load reduce HIV multiplication . . . ), and stop the progression of HIV disease. There are several classes of HIV drug, such as, for example, non-nucleoside reverse transcriptase inhibitors (NNRTIs), nucleoside reverse transcriptase inhibitors (NRTIs), post-attachment inhibitors (or entry inhibitors), protease inhibitors (PIs), CCR5 antagonists, integrase strand transfer inhibitors (INSTIs), fusion inhibitors (FIs).

In one embodiment, the antiretroviral (ART) agent is selected from the group consisting of Nucleoside reverse transcriptase inhibitors (NRTIs), Non-nucleoside reverse transcriptase inhibitors (NNRTIs), Protease inhibitors (PIs), Integrase inhibitors (INSTIs), Fusion inhibitors (FIs), Chemokine receptor antagonists (CCR5 antagonists) and Entry inhibitors (CD4-directed post-attachment inhibitors).

Non-limiting examples of antiretroviral (ART) agents include:

Nucleoside reverse transcriptase inhibitors (NRTIs) such as e.g.:
- Abacavir (Ziagen®)
- Didanosine (Videx®, Videx® EC)
- Emtricitabine (Emtriva)
- Lamivudine (Epivir®)
- Stavudine (Zerit®)
- Tenofovir disoproxil fumarate DF (Viread®)
- Tenofovir alafenamide AF
- Zidovudine (Retrovir®)

Non-nucleoside reverse transcriptase inhibitors (NNRTIs) such as e.g.:
- Delavirdine (Rescriptor®)
- Efavirenz (Sustiva®)
- Etravirine (Intelence®)
- Nevirapine (Viramune®, Viramune® XR)
- Rilpivirine (Edurant®)
- Doravirine (Pifeltro®)

Protease inhibitors (PIs) such as e.g.:
- Atazanavir (Reyataz®)
- Darunavir (Prezista®)
- Fosamprenavir (Lexiva®)
- Indinavir (Crixivan®)
- Lopinavir/ritonavir (Kaletra®)
- Nelfinavir (Viracept®)
- Ritonavir (Norvir®)
- Saquinavir (Invirase®)
- Tipranavir (Aptivus®)

Integrase inhibitors (INSTIs) such as e.g.:
- Raltegravir (Isentress®, Isentress® HD)
- Dolutegravir (Tivicay®)
- Elvitegravir (Vitekta®)

Chemokine receptor antagonist (CCR5 antagonist) such as e.g.
- Maraviroc (Selzentry®)

Fusion inhibitor (FI) such as e.g.
- Enfuvirtide (Fuzeon®)

Entry inhibitor such as e.g.
- Ibalizumab (Trogarzo®)

and any combination thereof.

In one embodiment, the ART agent according to the invention comprises several ART agents, or is a combination of several ART agents. These several ART agents are for instance chosen among the ART agents listed hereabove.

Generally, initial treatment regimens usually include two NTRIs combined with a third active antiretroviral drug, which may be in the INSTI, NNRTI, or PI class. They may sometimes include a booster, which may be cobicistat (Tybost®) or ritonavir (Norvir®).

In one embodiment, the ART agent according to the invention comprises a combination of at least two ART agents, preferably chosen among the ART agents listed hereabove.

In one embodiment, the ART agent according to the invention comprises a combination of two, three, four, five or six ART agents, preferably chosen among the ART agents listed hereabove.

ART combination products are known in the art and some of them are approved as complete daily regimens.

Non-limiting examples of antiretroviral (ART) agents which are combination ARTs or combined ARTs (cARTs) include the following ART combinations:
- Elvitegravir+cobicistat+emtricitabine+tenofovir DF (Stribild®)
- Elvitegravir+cobicistat+emtricitabine+tenofovir AF (Genvoya®)
- Darunavir+cobicistat+emtricitabine+tenofovir AF (Symtuza®)
- Rilpivirine+emtricitabine+tenofovir AF (Odefsey®)
- Rilpivirine+emtricitabine+tenofovir DF (Complera®)
- Bictegravir+emtricitabine+tenofovir AF (Biktarvy®)
- Dolutegravir+abacavir+lamivudine (Triumeq®)
- Dolutegravir+rilpivirine (Juluca®)
- Dolutegravir+lamivudine (Dovato®)
- Efavirenz+emtricitabine+tenofovir DF (Atripla®)
- Efavirenz+lamivudine+tenofovir DF (Symfi®)
- Doravirine+lamivudine+tenofovir DF (Delstrigo®)
- Emtricitabine+tenofovir AF (Descovy®)
- Emtricitabine+tenofovir DF (Truvada®)
- Abacavir+lamivudine (Epzicom®)
- Lamivudine+tenofovir DF (Cimduo®)
- Abacavir+lamivudine+zidovudine (Trizivir®)
- Zidovudine+lamivudine (Combivir®)
- Atazanavir+cobicistat (Evotaz®)
- Darunavir ethanolate+cobicistat (Prezcobix®).

One option for eradicating HIV-1 reservoirs is based on HIV-1 reactivation in latently-infected cells while maintaining antiretroviral therapy (ART) in order to prevent spreading of the infection by the neosynthesized virus. Several latency reversing agents (LRAs) with distinct mechanistic classes have been characterized to reactivate HIV-1 viral gene expression. Some LRAs have shown their potential to reverse HIV-1 latency in order to purge latent HIV-1.

Non-limiting examples of latency reversing agent (LRA) include:
- PKC agonists, which for instance act on NF-κB activation, such as e.g. Prostratin Bryostatin-1 Ingenols: Ingenol-B, Ingenol 3,20-dibenzoate (Ingenol-db), ingenol-3-angelate (ingenol mebutate, PEP005);
- MAPK agonist, which for instance act on MAP Kinase activation, such as e.g. Procyanidin trimer C1;
- CCR5 antagonist, which for instance act on NF-κB activation, such as e.g. Maraviroc;
- Tat vaccine, which for instance act on Activation of HIV-1 LTR, such as e.g. Tat Oyi vaccine, Tat-R5M4 protein;
- SMAC mimetics, which for instance act on Induction of non-canonical NF-κB pathways, such as e.g. SBI-0637142, Birinapant;
- Inducers of P-TEFb release, which for instance act on Release of P-TEFb, such as e.g. BETis: JQ1, I-BET, I-BET151, OTX015, UMB-136, MMQO, CPI-203, RVX-208, PFI-1, BI-2536 and BI-6727; HMBA;
- Activators of Akt pathway, which for instance act on Upregulation of Akt signaling pathway, such as e.g. Disulfiram;
- Benzotriazole derivatives, which for instance act on STAT5 activation, such as e.g. 1-hydroxybenzotriazol (HOBt);
- Epigenetic modifiers, which for instance act on HDAC inhibition, such as e.g. HDACis: TSA, trapoxin, SAHA, romidepsin, panobinostat, entinostat, givinostat, valproic acid, MRK-1/11, AR-42, fimepinostat, chidamide;
- Epigenetic modifiers, which for instance act on Suv39H1, G9a, SMYD2, such as e.g. HMTis: chaetocin, EPZ-6438, GSK-343, DZNEP, BIX-01294, UNC-0638;
- Epigenetic modifiers, which for instance act on DNMT1, 3a, 3b, such as e.g. DNMTis: 5-AzaC, 5-AzadC; and
- Immunomodulatory LRAs, such as e.g. TLR agonists: TLR2 (Pam3CSK4), TLR7 (GS-9620), TLR8, TLR9 (MGN 1703) agonists; IL-15 agonist (ALT-803); Immune checkpoint inhibitors: anti-PD-1 (nivolumab, pembrolizumab), anti-CTLA-4 (ipilimumab).

In some embodiments, the latency reversing agent (LRA) is selected from the group consisting of PKC agonists, MAPK agonists, CCR5 antagonists, Tat vaccines, SMAC mimetics, inducers of P-TEFb release, activators of Akt pathway, benzotriazole derivatives, epigenetic modifiers and immunomodulatory LRAs.

In some embodiments, the latency reversing agent (LRA) is a Prostratin Bryostatin-1 Ingenol, such as Ingenol-B, Ingenol 3,20-dibenzoate (Ingenol-db), ingenol-3-angelate (ingenol mebutate, PEP005); Procyanidin trimer C1; Maraviroc; Tat Oyi vaccine, Tat-R5M4 protein; SBI-0637142, Birinapant; a BETi such as JQ1, I-BET, I-BET151, OTX015, UMB-136, MMQO, CPI-203, RVX-208, PFI-1, BI-2536 and BI-6727 HMBA; Disulfiram; 1-hydroxybenzotriazol (HOBt); a HDACi such as TSA, trapoxin, SAHA, romidepsin, panobinostat, entinostat, givinostat, valproic acid, MRK-1/11, AR-42, fimepinostat, chidamide; a HMTi such as chaetocin, EPZ-6438, GSK-343, DZNEP, BIX-01294, UNC-0638; a DNMTi such as 5-AzaC, 5-AzadC; a TLR agonist such as a TLR2 agonist (Pam3CSK4), a TLR7 agonist (GS-9620), a TLR8 agonist, a TLR9 agonist (MGN 1703) agonist; an IL-15 agonist (ALT-803); and/or an immune checkpoint inhibitor such as anti-PD-1 (nivolumab, pembrolizumab), or anti-CTLA-4 (ipilimumab).

In one embodiment, the latency reversing agent according to the invention comprises several LRAs, or is a combination of several LRAs, which are for instance chosen among the LRAs listed hereabove.

In one embodiment, the latency reversing agent according to the invention comprises a combination of at least two LRAs, preferably chosen among the LRAs listed hereabove.

In one embodiment, the latency reversing agent according to the invention comprises a combination of two, three, four, five or six LRAs, preferably chosen among the LRAs listed hereabove.

In one embodiment, at least one agent comprised in the combination is comprised in a composition.

In one embodiment, one, two or three agents selected from:
a) an interferon-alpha (IFN-α) blocking agent,
b) a type III interferon blocking agent,
c) optionally, an interferon-beta (IFN-β) blocking agent,
are comprised in a single composition.

In one embodiment, one or two agents selected from:
d) an antiretroviral (ART) agent, and
e) optionally, a latency-reversing agent (LRA).
are comprised in a single composition.

In one embodiment, all agents comprised in the combination (i.e. agents a), b), c), d) and e)) are comprised in a composition.

In some embodiments, said composition consists essentially of the at least one agent of the combination according to the invention.

As used herein, "consisting essentially of", with reference to a composition, means that the at least one agent is the only therapeutic agent or agent with a biologic activity within said composition.

In one embodiment, said composition is a pharmaceutical composition and further comprises at least one pharmaceutically acceptable excipient.

As used herein, the term "excipient" refers to any and all conventional solvents, dispersion media, fillers, solid carriers, aqueous solutions, coatings, antibacterial and antifungal agents, isotonic and absorption delaying agents and the like. In general, the nature of the excipient will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. For human administration, preparations should meet sterility, pyrogenicity, general safety and purity standards as required by regulatory offices, such as, for example, FDA Office or EMA. In one embodiment, the excipient is an adjuvant, a stabilizer, an emulsifier, a thickener, a preservative, an antibiotic, an organic or inorganic acid or its salt, a sugar, an alcohol, an antioxidant, a diluent, a solvent, a filler, a binder, a sorbent, a buffering agent, a chelating agent, a lubricant, a coloring agent, or any other component By "pharmaceutically acceptable" is meant that the ingredients of a pharmaceutical composition are compatible with each other and not deleterious to the subject to which it is administered. Examples of pharmaceutically acceptable excipient include, but are not limited to, water, saline, phosphate buffered saline, dextrose, glycerol, ethanol and the like or combinations thereof.

Pharmaceutically acceptable excipients that may be used in the pharmaceutical combination of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

In one embodiment, said composition is a vaccine composition. In one embodiment, said vaccine composition further comprises at least one adjuvant.

Another object of the invention is a pharmaceutical composition comprising a combination of:
a) an interferon-alpha (IFN-α) blocking agent,
b) a type III interferon blocking agent,
c) optionally, an interferon-beta (IFN-β) blocking agent,
and at least one pharmaceutically acceptable excipient, for use in the treatment of AIDS in a subject in need thereof.

Another object of the invention is a pharmaceutical composition comprising a combination of:
d) an antiretroviral (ART) agent, and
e) optionally, a latency-reversing agent (LRA).
and at least one pharmaceutically acceptable excipient, for use in the treatment of AIDS in a subject in need thereof.

The different agents of the combination or kit-of-parts according to the invention (i.e. parts a), b), c), d) and e) of the combination) are to be administered either simultaneously, separately or sequentially with respect to each other.

According to one embodiment, the agent a), b), c), d) or e) of the combination, the combination, the kit-of-parts, the composition or the pharmaceutical composition of the invention is formulated for administration to the subject.

The expression "combined preparation" or "combination" refers to any preparation comprising at least two components, such as e.g. parts a), b), c), d) and/or e) of the combination of the invention. The different components of the combined preparation, or of the combination, may be used simultaneously, semi-simultaneously, separately, sequentially or spaced out over a period of time so as to obtain the maximum efficacy of the combination.

For instance, they may be administered concurrently, i.e. simultaneously in time, or sequentially, i.e. one component is administered after the other one(s). After administration of the first component, the other component(s) can be administered substantially immediately thereafter or after an effective time period. The effective time period is the amount of time given for realization of maximum benefit from the administration of the components.

As a result, for the purposes of the present invention, the combined preparations or combinations are not limited to those which are obtained by physical association of the constituents, but may also be in the form of separate products permitting a separate administration, which can be simultaneous or spaced out over a period of time.

Alternatively, the different components may be co-formulated.

In one embodiment, the agent a), b), c), d) or e) of the combination, the combination, the kit-of-parts, the composition or the pharmaceutical composition of the invention may be administered orally, intragastrically, parenterally, topically, by inhalation spray, rectally, nasally, buccally, preputially, vaginally or via an implanted reservoir.

In one embodiment, the administration of each part of the combination of the invention (i.e. agent a), b), c), d) or e) of the combination of the invention) can be done by the same route of administration or by a different route of administration.

In one embodiment, the administration of a) an interferon-alpha (IFN-α) blocking agent, b) a type III interferon blocking agent, and c) optionally, an interferon-beta (IFN-β) blocking agent, is done by a route of administration, and the administration of d) an antiretroviral (ART) agent and e) optionally, a latency-reversing agent (LRA) is done by another route of administration.

In one embodiment, the agent a), b), c), d) or e) of the combination, the combination, the kit-of-parts, the composition or the pharmaceutical composition of the invention is in an adapted form for an oral or an intragastric administration. Thus, in one embodiment, the agent a), b), c), d) or e) of the combination, the combination, the kit-of-parts, the composition or the pharmaceutical composition of the invention is to be administered orally or intragastrically to the subject, for example as a powder, a tablet, a capsule, and the like or as a tablet formulated for extended or sustained release or as an oral solution.

For instance, the antiretroviral (ART) agent and, optionally, the latency-reversing agent (LRA), are to be administered orally or intragastrically to the subject, for example as a powder, a tablet, a capsule, and the like or as a tablet formulated for extended or sustained release or as an oral solution.

Examples of forms adapted for oral or intragastric administration include, without being limited to, liquid, paste or solid compositions, and more particularly tablets, tablets formulated for extended or sustained release, capsules, pills, dragees, liquids, gels, syrups, slurries, suspensions, and the like.

In one embodiment, the antiretroviral (ART) agent and, optionally, the latency-reversing agent (LRA) are in an adapted form for an oral or intragastric administration. Thus, in one embodiment, the antiretroviral (ART) agent and, optionally, the latency-reversing agent (LRA) are to be administered orally or intragastrically to the subject, for example as a capsule or as a tablet or as an oral solution.

In another embodiment, the interferon-alpha (IFN-α) blocking agent, the type III interferon blocking agent and, optionally, the interferon-beta (IFN-β) blocking agent, are in an adapted form for an oral or intragastric administration. Thus, in one embodiment, the interferon-alpha (IFN-α) blocking agent, the type III interferon blocking agent and, optionally, the interferon-beta (IFN-β) blocking agent, are to be administered orally or intragastrically to the subject, for example as a capsule or as a tablet or as an oral solution.

In one embodiment, the agent a), b), c), d) or e) of the combination, the combination, the kit-of-parts, the composition or the pharmaceutical composition of the invention is in a form adapted for parenteral administration.

In another embodiment, the agent a), b), c), d) or e) of the combination, the combination, the kit-of-parts, the composition or the pharmaceutical composition of the invention is in an adapted form for an injection such as, for example, for intravenous, subcutaneous, intramuscular, intraperitoneal intradermal, transdermal injection or infusion. Thus, the agent a), b), c), d) or e) of the combination, the combination, the kit-of-parts, the composition or the pharmaceutical composition of the invention is to be injected to the subject, by intravenous, intramuscular, intraperitoneal, intrapleural, subcutaneous, transdermal injection or infusion.

A sterile injectable form may be a solution or an aqueous or oleaginous suspension. These suspensions may be formulated according to techniques known in the art using suitable dispersing or wetting agents and suspending agents. The sterile injectable preparation may also be a sterile injectable solution or suspension in a non-toxic pharmaceutically acceptable diluent or solvent. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In one embodiment, the interferon-alpha (IFN-α) blocking agent, the type III interferon blocking agent and, optionally, the interferon-beta (IFN-β) blocking agent, are in an adapted form for a parenteral administration and/or injection. Thus, in another embodiment, the interferon-alpha (IFN-α) blocking agent, the type III interferon blocking agent and, optionally, the interferon-beta (IFN-β) blocking agent, are to be administered parenterally and/or injected to the subject, by intravenous, intramuscular, intraperitoneal, intrapleural, subcutaneous, transdermal injection or infusion, preferably by intravenous injection.

In another embodiment, the antiretroviral (ART) agent and, optionally, the latency-reversing agent (LRA) are in an adapted form for a parenteral administration and/or injection. Thus, in another embodiment, the antiretroviral (ART) agent and, optionally, the latency-reversing agent (LRA) are to be administered parenterally and/or injected to the subject, by intravenous, intramuscular, intraperitoneal, intrapleural, subcutaneous, transdermal injection or infusion, preferably by intravenous injection.

Preferably, the interferon-alpha (IFN-α) blocking agent, the type III interferon blocking agent and, optionally, the interferon-beta (IFN-β) blocking agent, are in an adapted form for a parenteral administration and/or injection, and are to be administered parenterally and/or injected to the subject, by intravenous, intramuscular, intraperitoneal, intrapleural, subcutaneous, transdermal injection or infusion, preferably by intravenous injection.

Preferably, the antiretroviral (ART) agent and, optionally, the latency-reversing agent (LRA) are in an adapted form for an oral or intragastric administration, and are to be administered orally or intragastrically to the subject, for example as a capsule, a tablet or an oral solution.

The different agents of the combination or kit-of-parts according to the invention (i.e. parts a), b), c), d) and e) of the combination) are to be administered either simultaneously, separately or sequentially with respect to each other.

Parts a), b), c), d) and e) of the combination may be administered concurrently, i.e. simultaneously in time, or sequentially, i.e. administration of certain components of the combination followed by administration of other components of the combination. After administration of the first component(s), the other component(s) can be administered substantially immediately thereafter or after an effective time period. The effective time period is the amount of time given for realization of maximum benefit from the administration of the components.

In one embodiment, the interferon-alpha (IFN-α) blocking agent, the type III interferon blocking agent, optionally the interferon-beta (IFN-β) blocking agent, the antiretroviral (ART) agent and, optionally, the latency-reversing agent (LRA) are all administered at the same time.

In one embodiment, the IFN-α blocking agent, the type III interferon blocking agent, and optionally the interferon-beta (IFN-β) blocking agent are administered concurrently or simultaneously.

In one embodiment, the antiretroviral (ART) agent, and optionally the latency-reversing agent are administered concurrently or simultaneously.

In one embodiment, the interferon-alpha (IFN-α) blocking agent, the type III interferon blocking agent, and/or the interferon-beta (IFN-β) blocking agent, are to be administered prior to the antiretroviral (ART) agent and/or the latency-reversing agent (LRA).

In one embodiment, the antiretroviral (ART) agent and/or the latency-reversing agent (LRA) are to be administered prior to the interferon-alpha (IFN-α) blocking agent, the type III interferon blocking agent, and/or the interferon-beta (IFN-β) blocking agent.

In one embodiment, the subject receives one or more doses (one or more takes) of the IFN-α blocking agent, the type III interferon blocking agent, and/or the interferon-beta (IFN-β) blocking agent before starting receiving all parts a), b), c), d) and e) of the combination.

For instance, in a first period of time, the subject receives one or more doses (one or more takes) of the IFN-α blocking agent, the type III interferon blocking agent, and optionally the interferon-beta (IFN-β) blocking agent, during one or several weeks (e.g. 1, 2, 3, 4, 5, 6, 7, 8 or 10 weeks) in the absence of ART agent and LRA administration. Then, in a second period of time, the subject continues receiving administrations of the IFN-α blocking agent, the type III interferon blocking agent, and/or the interferon-beta (IFN-β) blocking agent, and also receives administrations of the antiretroviral (ART) agent, and optionally the latency-reversing agent.

Alternatively, in a first period of time, the subject receives one or more doses (one or more takes) of the antiretroviral (ART) agent, and optionally the latency-reversing agent, during one or several weeks or months (e.g. 1, 2, 3, 4, 5, 6, 7, 8, 10 or 12 weeks or months) in the absence of administration of IFN-α blocking agent, the type III interferon blocking agent, and/or the interferon-beta (IFN-β) blocking agent. Then, in a second period of time, the subject continues receiving administrations of the antiretroviral (ART) agent, and optionally the latency-reversing agent, and also receives administrations of the IFN-α blocking agent, the type III interferon blocking agent, and optionally the interferon-beta (IFN-β) blocking agent.

In one embodiment, the agent a), b), c), d) or e) of the combination, the combination, the kit-of-parts, the composition or the pharmaceutical composition of the invention is to be administered to the subject in need thereof in a therapeutically effective amount.

The term "therapeutically effective amount", as used herein, refers to an amount effective, at dosages and for periods of time necessary, to achieve a desired preventive and/or therapeutic result.

It will be however understood that the total daily usage of the agent a), b), c), d) or e) of the combination, the combination, the kit-of-parts, the composition or the pharmaceutical composition of the invention will be decided by the attending physician within the scope of sound medical judgment. The specific therapeutically effective dose level for any particular patient will depend upon a variety of factors including the disease being treated and the severity of the disease; activity of the specific agent(s), the combination, the kit-of-parts, the pharmaceutical composition or medicament employed; the age, body weight, general health, sex and diet of the subject; the time of administration, route of administration, and rate of excretion of the specific agent(s), the combination, the kit-of-parts, the pharmaceutical composition or medicament employed; the duration of the treatment; drugs used in combination or coincidental with the specific agent(s), the combination, the kit-of-parts, the pharmaceutical composition or medicament employed; and like factors well known in the medical arts. For example, it is well within the skill of the art to start doses of the compound at levels lower than those required to achieve the desired therapeutic effect and to gradually increase the dosage until the desired effect is achieved. The total dose required for each treatment may be administered by multiple doses or in a single dose.

In one embodiment, a therapeutically effective amount of one of the agents a), b), c), d) or e) of the combination of the invention ranges from about 0.1 mg/kg to about 10 mg/kg, from about 0.2 mg/kg to about 9 mg/kg, from about 0.3 mg/kg to about 8 mg/kg, from about 0.4 mg/kg to about 7.5 mg/kg, from about 0.5 mg/kg to about 7 mg/kg.

In one embodiment, a therapeutically effective amount of the interferon-alpha (IFN-α) blocking agent, the type III interferon blocking agent or the interferon-beta (IFN-β) blocking agent (i.e. of one of the agents a), b), c)) ranges from about 1 mg/kg to about 10 mg/kg, from about 2 mg/kg to about 9 mg/kg, from about 3 mg/kg to about 8 mg/kg, from about 4 mg/kg to about 7 mg/kg, from about 4 mg/kg to about 6 mg/kg.

In one embodiment, a therapeutically effective amount of one of the agent a), b), c), d) or e) of the combination of the invention ranges from about 1 mg to about 4000 mg, from about 10 mg to about 3000 mg, from about 25 mg to about 2000 mg, from about 50 mg to about 2000 mg, from about 100 mg to about 1500 mg, from about 200 mg to about 1000 mg.

In one embodiment, a therapeutically effective amount of the antiretroviral (ART) agent or of the latency-reversing agent (LRA) (i.e. of one of the agents d) or e)) ranges from about 1 mg to about 4000 mg, from about 10 mg to about 3000 mg, from about 25 mg to about 2000 mg, from about 50 mg to about 2000 mg, from about 100 mg to about 1500 mg, from about 200 mg to about 1000 mg.

Usually, there is a set time interval between separate administrations of the agent a), b), c), d) or e) of the combination, the combination, the kit-of-parts, the composition or the pharmaceutical composition of the invention. While this interval varies for every subject, typically it ranges from 1 days to several weeks, and is often 1, 2, 4, 6 or 8 days, or 1, 2, 4, 6 or 8 weeks. In one embodiment, the administration regimes typically have from 1 to 20 administrations of the different parts of the combination of the invention, but may have as few as one or two or four or eight or ten. In another embodiment the administration regimes is annual, biannual or other long interval (5-10 years).

In one embodiment, a therapeutically effective amount of the agent a), b), c), d) or e) of the combination, the combination, the kit-of-parts, the composition or the pharmaceutical composition of the invention is to be administered once a day, twice a day, three times a day or more.

In one embodiment, a therapeutically effective amount of the agent a), b), c), d) or e) of the combination, the combination, the kit-of-parts, the composition or the pharmaceutical composition of the invention is to be administered every day, every two days, every three days, every four days, every five days, every six days.

In one embodiment, a therapeutically effective amount of the agent a), b), c), d) or e) of the combination, the combination, the kit-of-parts, the composition or the pharmaceutical composition of the invention is to be administered every week, every two weeks, every three weeks, every four weeks, every five weeks.

In one embodiment, a therapeutically effective amount of the agent a), b), c), d) or e) of the combination, the combination, the kit-of-parts, the composition or the pharmaceutical composition of the invention is to be administered every month, every two months, every three months, every four months, every five months, every six months.

In one embodiment, a therapeutically effective amount of the agent a), b), c), d) or e) of the combination, the combination, the kit-of-parts, the composition or the pharmaceutical composition of the invention is to be administered every 12 hours, every 24 hours, every 36 hours, every 48 hours, every 60 hours, every 72 hours, every 96 hours.

In a preferred embodiment, a therapeutically effective amount of the interferon-alpha (IFN-α) blocking agent, the type III interferon blocking agent or the interferon-beta (IFN-β) blocking agent (i.e. of one of the agents a), b), c)) is to be administered every week, every two weeks, every three weeks, every four weeks, every five weeks, preferably every two weeks.

In a preferred embodiment, a therapeutically effective amount of the antiretroviral (ART) agent or of the latency-reversing agent (LRA) (i.e. of one of the agents d) or e)) is to be administered daily, for instance once a day, twice a day, or three times a day.

In a preferred embodiment, a therapeutically effective amount of the antiretroviral (ART) agent or of the latency-reversing agent (LRA) (i.e. of one of the agents d) or e)) is a daily dose to be administered in one, two, three or more takes or in one, two, three or more injections.

In one embodiment, the agent a), b), c), d) or e) of the combination, the combination, the kit-of-parts, the composition or the pharmaceutical composition of the invention is for acute administration. Preferably, the agent a), b), c), d) or e) of the combination, the combination, the kit-of-parts, the composition or the pharmaceutical composition of the invention is for chronic administration.

In one embodiment, a therapeutically effective amount of the agent a), b), c), d) or e) of the combination, the combination, the kit-of-parts, the composition or the pharmaceutical composition of the invention is to be administered for a period of time ranging from about two weeks to about twenty-four weeks, from about two weeks to about twelve weeks, from about two weeks to about six weeks.

In one embodiment, a therapeutically effective amount of the agent a), b), c), d) or e) of the combination, the combination, the kit-of-parts, the composition or the pharmaceutical composition of the invention is to be administered for about 1 month, 2 months, 3 months, 6 months, 1 year or more.

Alternatively, a therapeutically effective amount of the agent a), b), c), d) or e) of the combination, the combination, the kit-of-parts, the composition or the pharmaceutical composition of the invention is to be administered to the subject until no cell containing replication-competent proviral HIV DNA is detected in a blood sample from the subject.

Indeed, in one embodiment, the method of treatment of the invention further comprises assessing the presence of cells containing replication-competent proviral HIV DNA in a blood sample from the subject.

In another embodiment, the presence of cells containing replication-competent proviral HIV DNA is assessed in a blood sample from the subject.

In some embodiments, a therapeutically effective amount of the agent a), b), c), d) or e) of the combination, the combination, the kit-of-parts, the composition or the pharmaceutical composition of the invention is to be administered to the subject until no cell containing replication-competent proviral HIV DNA is detected in a blood sample from the subject.

Cells containing replication-competent proviral HIV DNA, also called "resistant cells" or "reservoir cells" may be detected in a sample, or their quantity, level or frequency in a sample may be measured by various assays known by the person skilled in the art.

For instance, cells containing replication-competent proviral HIV DNA may be detected in a sample, or their quantity, level or frequency in a sample may be measured by ex vivo viral outgrowth assay.

For example, plasma HIV-1 RNA levels, size of the HIV reservoir and/or CD4+ T cell count may be typically monitored for instance every 2 weeks, after collection of blood samples, 1 day before administration of the interferon-blocking agents (i.e. parts a), b) and c) of the combination described herein).

Plasma HIV-1 RNA levels may for instance be determined using the Roche COBAS AmpliPrep/COBAS TaqMan HIV-1 Assay (version 2.0) or the Roche cobas HIV-1 quantitative nucleic acid test (cobas 6800), which quantitate HIV-1 RNA over a range of $2 \times 10^1$ to $1 \times 10^7$ copies/ml.

Size of the HIV reservoir may for instance be assessed with Quantitative Viral Outgrowth Assay (QVOA).

QVOA may typically be performed as previously described in Huang S H et al, 2018 J Clin Invest 128:876-889. Briefly, isolated CD4$^+$ T cells may typically be plated out in serial dilutions (e.g. 2, 1, 0.5, 0.2, and 0.1 million per well), for instance into 12 wells in 24-well plates with added phytohemagglutinin (PHA; e.g. 2 µg/ml) and irradiated HIV-negative donor PBMC (e.g. $2 \times 10^6$ cells/well) to reactivate the infected cells. MOLT-4 CCR5 cells (e.g. $2 \times 10^6$ cells/well) may typically be added after 2 days of culture, to amplify the HIV. The p24 antigen in the culture supernatant may typically be quantified after 2 weeks of culture, for instance using an HIV p24 antigen enzyme-linked immunosorbent assay (ELISA) kit (Perkin-Elmer, Hopkinton, MA). Estimated frequencies of cells with replication-competent HIV-1 may typically be calculated using limiting dilution analysis.

CD4+ T-cell counts may for instance be determined by a clinical flow cytometry assay.

As a non-limiting example, administration of the interferon-blocking agents (i.e. parts a), b) and c) of the combination described herein) may be stopped when no cells with replication-competent HIV-1 are detected following 2-3 consecutive limiting dilution virus outgrowth assays (VOA).

As a non-limiting example, administration of the antiretroviral (ART) agent or/and the latency-reversing agent (LRA) (i.e. parts d) and/or e) of the combination described herein) may be stopped when no cells with replication-competent HIV-1 are detected with 3-4 consecutive limiting dilution virus outgrowth assays (VOA).

It will be apparent to the person skilled in the art that such timing in the treatment interruption is flexible.

In some cases, if viral clearance was not complete, AIDS symptoms (or a detectable viral load) may appear anew after a certain time after interruption of the treatment, such as e.g. after a few months, 6 months, 1 year, 2 years, 3 years, 4 years, 5 years, etc. after interruption of the treatment. In these cases, treatment with the combination of the invention may then be resumed after a certain time of treatment interruption.

Thus, in one embodiment, the combination of the invention is administered to the subject for a first period of time, then said treatment is interrupted during a period of time of a few months, 6 months, 1 year, 2 years, 3 years, 4 years, 5 years, 8 years or 10 years, and then the combination of the invention is administered anew to the subject for a second period of time, for instance until no cell containing replication-competent proviral HIV DNA is detected in a blood sample from the subject.

The subject may thus alternate between periods of time during which he receives administrations of the combination described herein and periods of time of treatment interruption.

The combination, the kit-of-parts, the composition or the pharmaceutical composition as described herein may be used alone.

Thus, in one embodiment, the combination, the kit-of-parts, the composition or the pharmaceutical composition as described herein is used alone and comprises a therapeutically effective dose of each part each part of the combination (i.e. agent a), b), c), d) or e)).

In another embodiment, the combination, the kit-of-parts, the composition or the pharmaceutical composition as described herein is used in combination with at least one further therapeutic agent.

Such administration may be simultaneous, separate or sequential. For simultaneous administration the agents may be administered as one composition or as separate compositions, as appropriate. The further therapeutic agent is typically relevant for disorders to be treated.

EXAMPLES

The present invention is further illustrated by the following examples.

Example 1: Effects of Type I and Type III Interferons on Innate and Adaptative Immune Responses Materials and Methods
Human Cell Lines HCC HepG2 and normal kidney epithelial Vero cell lines were obtained from ATCC. Cells were grown in Dulbecco's Modified Eagle Medium supplemented with 10% heat-inactivated Fetal Bovine Serum, 2 mM L-glutamine, 1% penicillin and streptomycin solution in hypoxia 2%. Cancer cell lines were grown to 70-100% confluency, subsequently passaged for a maximum of 5 times and freshly thawed thereafter. Cells were detached by means of accutase, resuspended in FBS-containing medium and collected by means of centrifugation (300 g, 3 min). Cell numbers were determined by means of trypan blue.
Human Blood Sample Blood samples from healthy individuals originated from Etablissement Francais du Sang (EFS, Paris). Blood cells are collected using standard procedures.
Cell Purification and Culture Peripheral blood mononuclear cells (PBMCs) are isolated by density gradient centrifugation on Ficoll-Hypaque (Pharmacia). PBMCs are used either as fresh cells or stored frozen in liquid nitrogen. T-cell subsets and T cell-depleted accessory cells (ΔCD3 cells) are isolated from either fresh or frozen PBMCs. T cell-depleted accessory cells (ΔCD3 cells) are isolated by negative selection from PBMCs by incubation with anti-CD3-coated Dynabeads (Dynal Biotech) and are irradiated at 3000 rad (referred to as ΔCD3-feeder). CD4$^+$ T cells are negatively selected from PBMCs with a CD4$^+$ T-cell isolation kit (Miltenyi Biotec), yielding CD4$^+$ T-cell populations at a purity of 96-99%. T cell subsets are cultured either in IMDM supplemented with 5% SVF, 100 IU/ml penicillin/streptomycin, 1 mM sodium pyruvate, 1 mM nonessential amino acids, glutamax and 10 mM HEPES (IMDM-5 media) in hypoxia 2%.
Freezing and Thawing of Cells Cells were frozen in FBS containing 10% DMSO. Cryo tubes were placed in CoolCell (Biocision) freezing containers and incubated at −80° C. After 2 days tubes were transferred to liquid nitrogen and stored until required. Thawing of cells was performed by placing cryo tubes in a 37° C. water bath for approximately 30 seconds. Next, cell suspension was mixed with equivalent volume of pre-warmed media and subsequently transferred to falcon tubes containing the same medium. Cells were pelleted by centrifugation (300 g, 3 min) to remove DMSO. The cell pellet was resuspended in cell culture medium
Real-Time PCR for ISGs Detection HepG2 cells were seeded at a density of 2×10$^5$ cells per well in 12-well plates and incubated for 24 h. Then, fresh media was added with the indicated interferons. The cells were incubated for 4 h and then lysed, and RNA was purified using an extraction kit (Qiagen), according to the manufacturer's instructions. Synthesis of cDNA was performed using the PrimeScript RT Reagent kit (TAKARA). Quantitative PCR was carried out using the Power SYBR Green PCR Master Mix (Applied Biosystems) on a LightCycler 480 instrument (Roche). Each reaction was carried out in duplicate in a total volume of 100 µL. Primers were designed to be intron-spanning using Primer3 or Primer Express® v3.0 software (Applied Biosystems). To measure the cellular transcriptional response to IFN stimulation, 3 ISG targets, MXI, OASL and ISG15, were selected based on published results investigating the transcriptional response in IFN-stimulated PBMCs (see, for example, Waddell et al. (2010) PLoS One. 5(3):e97532). For gene induction assays, fold change values were calculated using the ΔΔCt method. The geometric mean of the Ct values of the reference genes, S14, was used as a reference value.
Virus Production The virus used EMCV (FA strain) was grown on monolayers of Vero cells to complete cytopathic effect or until all cells were affected by the infection as determined by microscopy and prepared by two cycles of freezing and thawing, followed by centrifugation for 30 min at 5,000×g for removal of cellular debris.
Antiviral Assay Antiviral assays were done on HepG2 cells, which were seeded in DMEM supplemented with 10% FCS at a density of 1.5×10$^4$ in 96-well plates and left to settle. The cells were incubated with indicated doses of IFNs for 24 h before challenge with EMCV. The cells were incubated with virus for 48 h. The medium was removed between each step. The viability of the cells was analyzed by a bioassay based on the dehydrogenase system; this system in intact cells will convert the substrate, MTT, into formazan (blue), which in turn can be measured spectrophotometrically. Briefly, the cells were given MTT and incubated for 2 h. An extraction buffer (containing 6 to 11% sodium dodecyl sulfate and 45% N,N-dimethylformamide) was added to the cells, and the cells were then incubated overnight at 37° C. Subsequently, the absorbance at 570 nm was determined employing the extraction buffer as the blank probe. A570 was directly proportional to antiviral activity.
Flow Cytometry Analysis CD3$^+$ T cells staining: anti-CD4 (SK3)-APC, anti-CD3 (UCHT1)-FITC, anti-CD8 (RPA-T8)-BV421 are from Becton Dickinson. Cells are stained for surface markers (at 4° C. in the dark for 30 min) using mixtures of Ab diluted in PBS containing 3% FBS, 2 mM EDTA (FACS buffer).

STAT1 Signaling Analysis:

Flow cytometry analysis of STAT1 phosphorylation (pSTAT1) was conducted in CD4+ T cells by using BD Phosflow technology according to the manufacturer's instructions (BD Bio-sciences, San Jose, CA). CD4+ T cells were stimulated by incubation with interferon type I and Type III at 37° C. for 20 min or left untreated. Activation was stopped by fixation using BD Phosflow Lyse/Fix Buffer (BD Biosciences) and cells were permeabilized with BD Perm Buffer III (BD Biosciences). Cells were stained with antibody recognizing specific phosphorylated STAT tyrosines: p-STAT1 (Y701)-PE. In multiparametric immunophenotyping experiments, cells were simultaneously stained with anti-CD3-FITC and 7-AAD. Increases in pSTAT1 were assayed as a ratio of induction over baseline levels (MFI fold change=MFI cytokine-stimulated/MFI untreated cells)

CFSE Staining:

CD4+ T cells were stained with 1 μM CFSE (CellTrace cell proliferation kit; Molecular Probes/Invitrogen) in PBS for 8 min at 37° C. at a concentration of 1.107 cells/ml. The labeling reaction was stopped by washing twice the cell with RPMI-1640 culture medium containing 10% FBS. The cells were then re-suspended at the desired concentration and subsequently used for proliferation assays.

7-AAD Staining:

Apoptosis of stimulated CFSE-labeled CD4+ T was determined using the 7-AAD assay. Briefly, cultured cells were stained with 20 μg/mL nuclear dye 7-amino-actinomycin D (7-AAD; Sigma-Aldrich, St-Quentin Fallavier, France) for 30 minutes at 4° C. FSC/7-AAD dot plots distinguish living ($FSC^{high}$/7-AAD$^-$) from apoptotic ($FSC^{high}$/7-AAD$^+$) cells and apoptotic bodies ($FSC^{low}$/7-AAD$^+$) and debris (($FSC^{low}$/7-AAD$^-$). Living cells were identified as CD3+ 7-AAD- FSC+ cells.

Appropriate isotype control Abs are used for each staining combination. Samples are acquired on a BD LSR FORTESSA flow cytometer using BD FACSDIVA 8.0.1 software (Becton Dickinson). Results are expressed in percentage (%) or in mean fluorescence intensity (MFI).

Functional Assay

T Cell Proliferation:

T cell proliferation was assessed with CFSE-dilution assays. For CFSE-dilution assay, at coculture completion, stimulated CFSE-labeled CD4+ T cells were harvested, co-stained with anti-CD3 mAb and 7-AAD, and the percentage of proliferating cells (defined as CFSE low fraction) in gated CD3+ 7-AAD- cells was determined by flow cytometry.

T Cell Activation:

CD38 Median Fluorescence Intensity (MFI) of CD38 expression was measured by flow cytometry in CD3+ 7-AAD-CFSE+ stimulated CD4+ T cells at the end of the culture.

CD4+ T Cell Polyclonal Stimulation:

CFSE-stained CD4+ T cells ($5 \times 10^4$/well) were cultured in 96 round-bottomed microwells in the presence of ΔCD3-feeder ($1 \times 10^5$/well) and plate-bound anti-CD3 Ab (2 μg/ml), soluble anti-CD28 mAb (2 μg/ml). CD4+ T cell proliferation was evaluated with CFSE dilution assays as described above by flow cytometry. Cells were stimulated in presence of different amounts of recombinant cytokines.

Allogeneic Mixed Lymphocyte Reaction:

CFSE-stained CD4+ T cells ($5 \times 10^4$/well) were cultured in 96 round-bottomed microwells in the presence of allogeneic mature DC. Proliferation of allo-activated CD4+ T cells with CFSE dilution assays as described above by flow cytometry. Cells were stimulated in presence of different amounts of recombinant cytokines.

Stat1 Phosphorylation Analysis:

CD4+ T cells were stimulated with IFN-λ1, INF-λ2, INF-λ3, IFN-λ4, or IFN-α2a (10 ng/ml) for 20 min, or were left unstimulated (control). Phosphorylated Stat1 levels was assessed by flow cytometry as described above.

Results

Type I interferons (IFN-α/β) and the more recently identified type III IFNs (IFN-λ) function as the first line of defense against virus infection, and regulate the development of both innate and adaptive immune responses. Type III IFNs were originally identified as a novel ligand-receptor system acting in parallel with type I IFNs, but subsequent studies have provided increasing evidence for distinct roles for each IFN family.

The inventors aimed to evaluate the effects of type I and type III interferons on both innate (antiviral) and adaptive immune response (CD4+ T cell proliferation).

Antiviral Activities of Types I and III

The ability of IFN type I and III to induce the expression of interferon-stimulated genes (ISGs) was analyzed by qPCR.

Briefly, the antiviral activity of type I and III was tested in HepG2 cells treated with IFN-α2a, IFNλ1, IFNλ3 or IFNλ4 for 4 hours. Then the induction of the well-known interferon-stimulated genes (ISGs) MX1, IFIT1 and OASL was monitored by qPCR.

As shown in FIG. 1A, all five interferons clearly induced all three ISGs.

Since the investigated ISGs are functionally related to an antiviral defense, the inventors further evaluate the capacity of both IFN to protect HepG2 cells from EMCV-induced cytopathogenic effect.

Briefly, cells were seeded in a 96-well microtiter plate and treated with the indicated amount of IFNs for 24 h and then challenged with EMCV for 20 h. Cell survival was measured by an MTT coloring assay.

As shown in FIG. 1B, IFN type III and IFN-α2a have intrinsic cellular antiviral activity and are able to fully protect HepG2 cells challenged with EMCV.

Anti Proliferative Activity of Type I and Type III Interferons Against CD4+ T Cells Proliferation The effect of IFN-type I and IFN type III on CD4+ T cells proliferation in response either to polyclonal or to allogeneic stimulation was evaluated in a mixed lymphocyte reaction (MLR) assay.

Briefly, CFSE labelled CD4+ T cells were first stimulated with poly I:C matured allogeneic dendritic cells in presence of different dose of IFNs. At 5 days post activation, the CFSE fluorescence dilution was analyzed.

Figure 2:
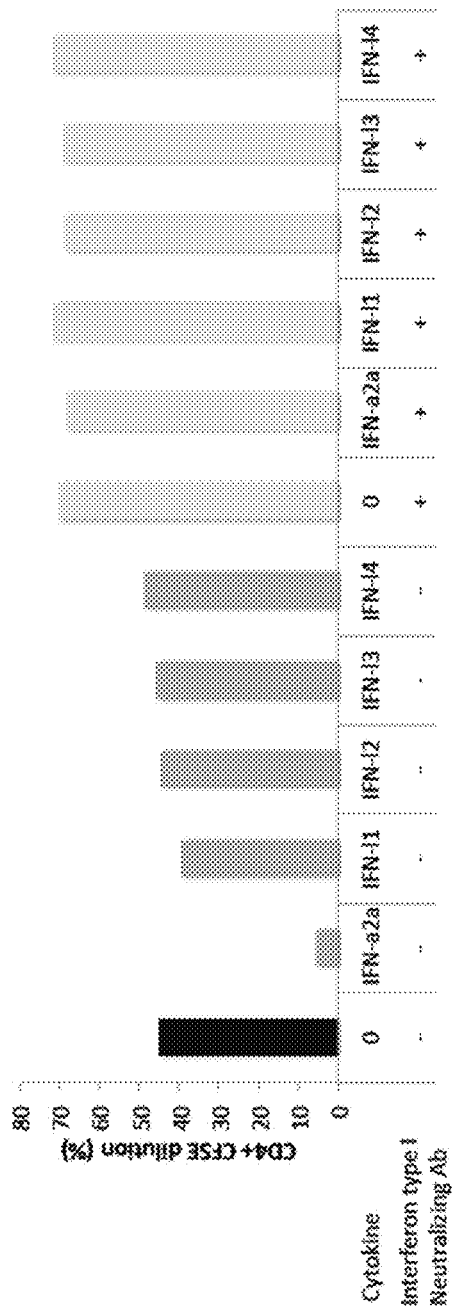
FIG. 2. Anti-proliferative activity of type I and type III interferons against CD4$^+$ T cells. CFSE-stained CD4$^+$ T cells ($10\times10^4$/well) were stimulated for 5 days in 96 round-bottomed microwells with allogeneic poly I:C matured DC in absence (control) or presence of 10 ng/ml of IFN-α2a, or IFNλ1 or IFNλ2 or IFNλ3 or IFNλ4. When indicated, anti-interferon type I receptor antibody was added. The percentage of CFSE dilution was evaluated by flow cytometry.

As shown in FIG. 2, IFN-α2a inhibits the proliferation of stimulated CD4+ T cells, while IFN type III exhibits no ability to suppress their proliferation. Of note, when the MLR was performed in the presence of anti-interferon type I receptor antibody, CD4+ T cells exhibit a greater proliferation. Thus, IFN-type I but not IFN type III inhibit the proliferation of allo-activated CD4+ T cells.

Moreover, the analysis of mRNA levels of the interferon-induced genes (ISG), IFIT1, MX1 and OASL in IFNs treated CD4+ T cells confirmed the lack or minimal sensitivity of CD4+ T cells to interferon type III.

Figure 3:
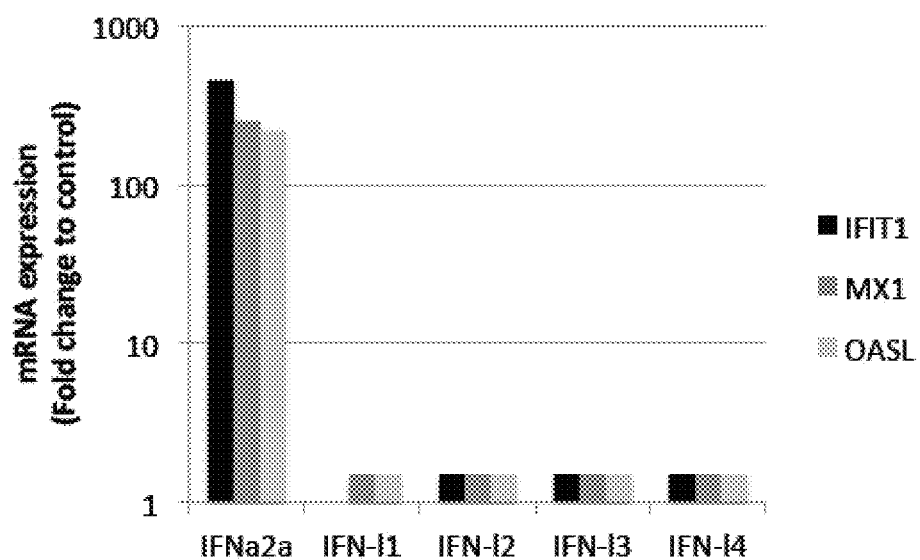
FIG. 3. IFN-α2a but not IFN-type III induces the expression of ISGs in CD4$^+$ T cells. CD4$^+$ T cells were treated with IFNα2a or IFNλ1/2/3/4 (10 ng/ml). After 4 h of stimulation, qRT-PCR were used to examine the mRNA levels of the interferon-induced genes, IFIT1, MX1 and OASL and fold-changes was calculated by $2^{-\Delta\Delta Ct}$ method as compared with non-treated cell control and using endogenous S14 mRNA level for normalization.

Indeed, as shown in FIG. 3, ISGs are induced only in CD4+ T cells stimulated with IFN-α2a. Thus, IFN-α2a but not IFN-type III induce the expression of ISGs in CD4+ T cells.

Because the Jak-STAT1/2 pathway being the major regulators of the transcription of ISG, the inventors have analyzed the phosphorylation levels of Stat1 proteins in response to IFN-type I, or interferon type III within CD4$^+$ T cells.

Figure 4:
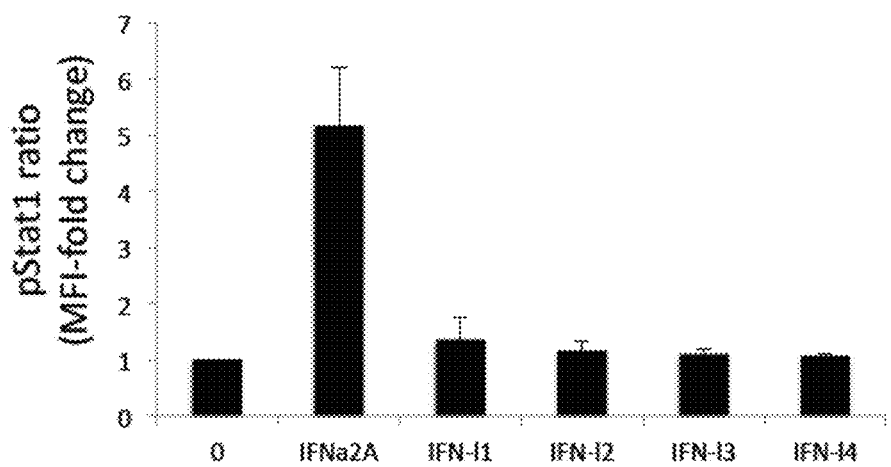
FIG. 4. IFN-α2a but not IFN-type III stimulates the phosphorylation of Stat1 in CD4$^+$ T cells. CD4$^+$ T cells were stimulated with 10 ng ml$^{-1}$ of IFN-λ1, IFN-λ2, INF-λ3, IFN-λ4, or IFN-α2a for 20 min, or were left unstimulated (control). Increases in pSTAT1 were evaluated as a ratio of induction over baseline levels (MFI fold change=MFI cytokine-stimulated/MFI untreated cells)

As shown in FIG. 4, only IFN-α2a was able to stimulate the phosphorylation of Stat1 within CD4$^+$ T cells. Therefore, IFN-α2a but not IFN-type III induces tyrosine phosphorylation of STAT1 in CD4$^+$ T cells.

Induction of Chronic Immune Activation in Presence of Type I and III Interferons.

Because chronic immune activation has been reasoned to be a significant contributor to disease progression in HIV-1-infected subjects, it is possible to monitor disease progression by measuring the expression of activation markers on CD4$^+$ T cell surface. Thus, the inventors have evaluated, by flow cytometry, the capacity of both IFNs to increase the CD38 expression on stimulated CD4$^+$ T cells.

Figure 5:
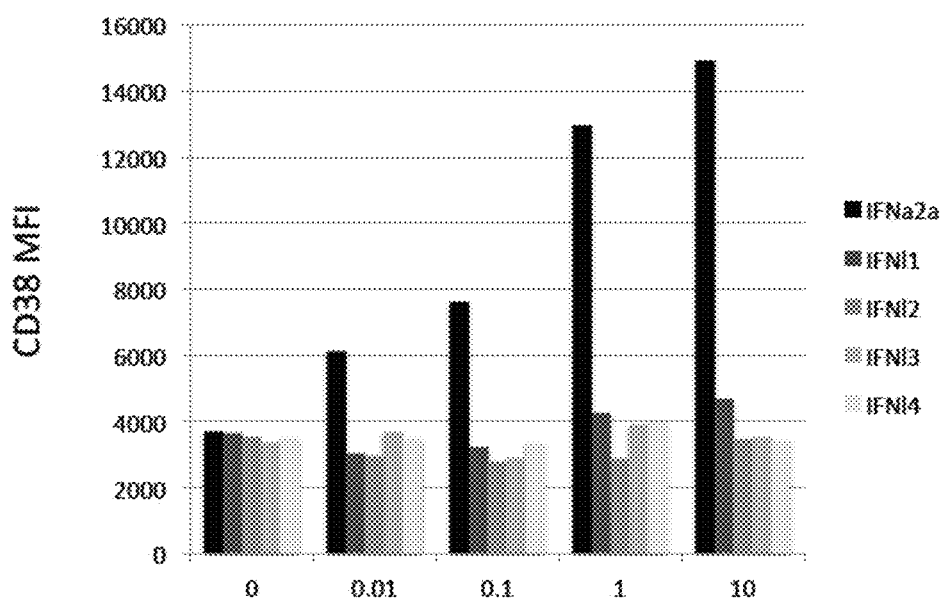
FIG. 5. IFN-α2a but not IFN-type III increases CD38 expression in CD3/CD28 stimulated CD4$^+$ T cells. CFSE-stained CD4$^+$ T cells ($4\times10^4$/well) were cultured in 96 round-bottomed microwells in the presence of ΔCD3-feeder ($4\times10^4$/well) and plate-bound anti-CD3 mAb (2 µg/ml), soluble anti-CD28 mAb (2 µg/ml) with increasing dose of IFN-α2a or IFN type III. CD38 Median Fluorescence Intensity (MFI) was measured by flow cytometry in CD3$^+$ 7-AAD-CFSE$^+$ stimulated CD4$^+$ T cells at the end of the culture.

As shown in FIG. 5, only IFN-α2a was able to enhance the expression of CD38 on stimulated CD4$^+$ T cells.

Collectively, these ex vivo experiments show that while exhibiting anti-viral activity, as does IFN-α, interferon type III, by contrast to the immunosuppressive IFN-α have no effect on CD4$^+$ T cell activation and proliferation. Indeed, interferon type III do not inhibit the initiation of the adaptative immune reaction as do IFN-α2a.

In conclusion, while interferon type I and type III are induced by the same viral stimulating factors and exhibit similar signature profiles, their biological activity appears not redundant but rather complementary. Indeed, following viral infection, during the innate phase of the immune response, interferons type III exert their antiviral effects in mucosal sites whereas IFN-α act more systemically in the whole organism. Furthermore, the subsequent adaptive immune reaction is inhibited at its initiation level by the immunosuppressive effect of the IFN-α on activated CD4$^+$ T cells.

Example 2: Critical Pathogenic Role of IFN-α and IFN-λ in Human HIV-1 Infection

Material and Methods

Cryopreserved PBMCs were thawed in RPMI 1640 with 10% fetal bovine serum (FBS) and washed in FACS buffer. Phenotypic staining was performed on 10$^6$ cells by incubation with a viability marker (AmCyan live-dead kit from Invitrogen) and with antibodies conjugated to CD3, CD4, CD8, CD45RA, CCR7. Subsequently, cells were washed, fixed with 4% paraformaldehyde for 5 min, washed, and acquired with an AURORA cytometer (Cytek).

Peripheral Blood samples were obtained either from healthy donors through Etablissement Francais du Sang (EFS, Paris, France) or from Elite controller HIV-1 patients and chronically-HIV-infected patients pre and post combined ART treatment.

Blood cells were collected using standard procedures. The study was performed according to the Helsinki declaration, and the study protocol was reviewed and approved by the local Ethics Committee. All samples were de-identified prior to use in this study.

Frozen serums were thawed at 4° C. and centrifuged at 4000 G for 10 min at 4° C. IFN-α and IFN-λ (IL-28A) serum concentrations were measured using the high sensitivity Single-Molecule Array (Simoa®) technology (Digital ELISA technology) (Quanterix) according to the manufacturer's instructions.

Results

Comparison of Central Memory (CM) CD8+ T Cell Distributions in HIV-1-Infected Subjects In study of chronically HIV-1-infected subjects, the following groups were studied:

(i) elite controllers (EC) who naturally suppress HIV-1 in the absence of combined antiretroviral therapy treatment (c-ART)

(ii) non-controllers before (pre-cART) and after cART (post-cART) treatment, and (iii) a cohort of age-matched healthy donor (HD) subjects.

The relative frequencies of the CM populations within the CD8+ T cell compartments were evaluated in each of the subject groups.

The gating strategy to define this subset is the following. Briefly, singlet cells were defined, followed by gating on lymphocytes and live cells. Among the live cells, CD3+ T lymphocytes were identified, followed by the definition of CD8+ subpopulations. Subsequently, the expression of CD45RA and CCR7 was analyzed in the CD8+ T lymphocytes. Central memory T cells (TCM) are CD45RA− CCR7+.

Figure 6:
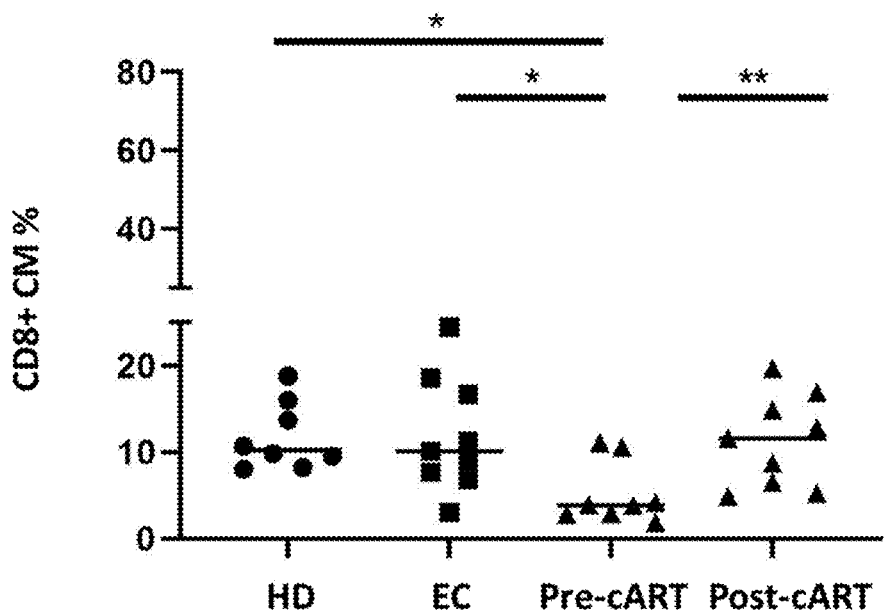
FIG. 6. Comparison of CM CD8+ T cell distributions and serum IFN-α levels in HIV-1-infected subjects and critical pathogenic role of IFN-α in human HIV-1 infection. (A) Comparison of CM CD8+ T cell distributions in HIV-1-infected subjects; (B) Comparison of serum IFN-α levels in HIV-1-infected subjects; (C) Relationship between CD8+ CM frequency and serum IFN-α level in non-treated HIV patients (EC and pre-cART group).
Figure 6:
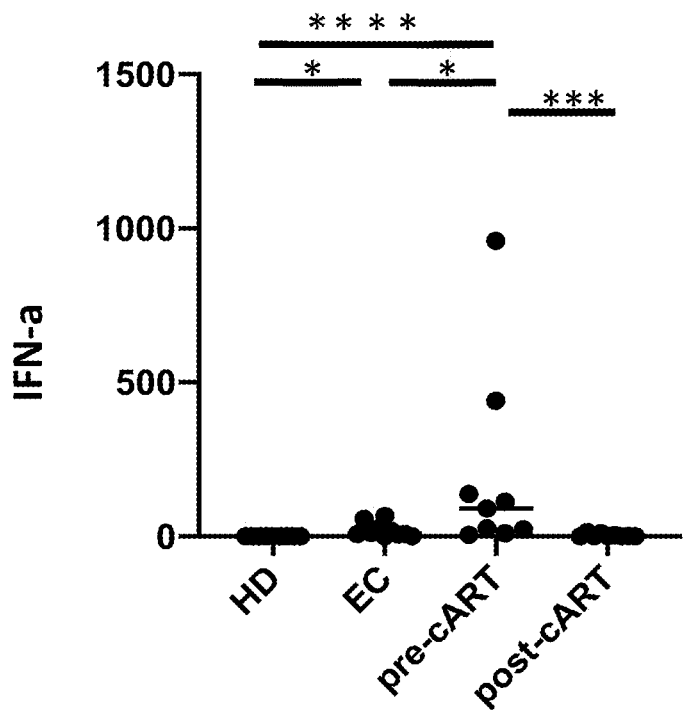
Figure 6:
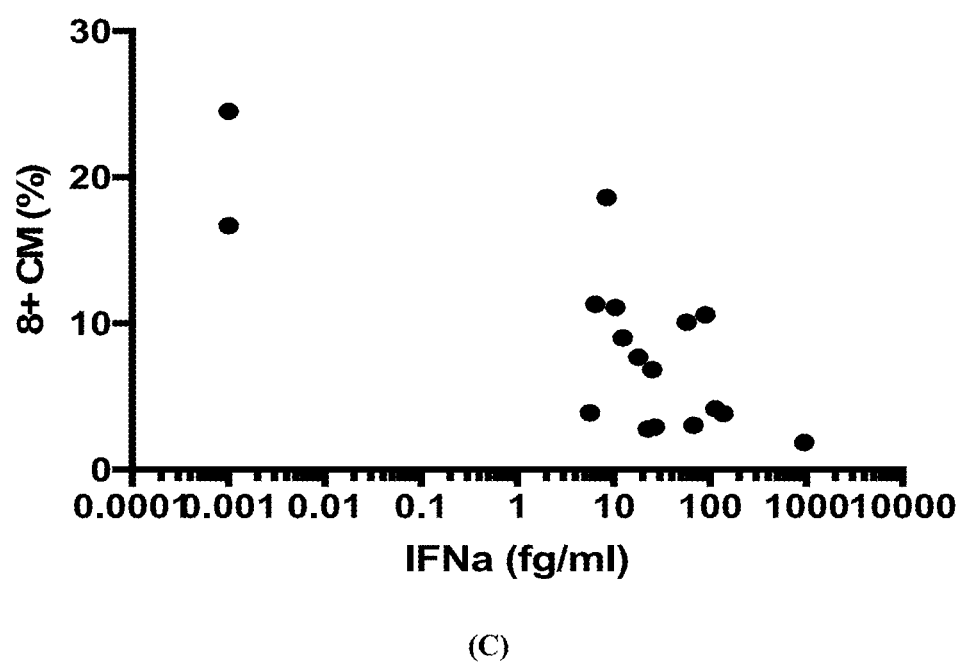

FIG. 6A shows that the level of CM CD8+ cells was significantly lower in non-controllers before cART than in other groups. Moreover, combined antiretroviral therapy (cART) results in increase of CM CD8+ cells.

Comparison of Serum IFN-α Levels in HIV-1-Infected Subjects

Serum levels of IFN-α was measured in the 4 groups. FIG. 6B shows that the non-controller patients have significantly increased serum IFN-α levels before treatment compared with after treatment.

IFN-α Inversely Correlates with the Percentage of CM CD8+ Cells in HIV-Infected Patients without Treatment In the population of HIV infected patients (EC pre-cART patients), the inventors explored the potential correlations between the level of CM CD8+ cells and the serum IFN-α levels. In this study, there was a significant negative correlation between the frequency of CM CD8+ cells and serum IFN-α levels (spearman correlation r=−0.667; p<0.005). This reflects the critical pathogenic effect of IFN-α on T cell proliferation in secondary organs (see FIG. 6C).

Comparison of Serum IFN-λ Levels in HIV-1-Infected Subjects

Serum from healthy control donors and HIV-1 infected patients, before and after cART treatment, originating from two distinct institutes were assayed by Simoa® for IFN-α and IFN-λ2 proteins.

Before cART treatment, serum levels of both IFN-α and IFN-λ were higher in patients versus controls. After cART treatment, the levels of IFN-α had decreased but the levels of IFN-λ remained unchanged (FIG. 7A) or increased slightly (FIG. 7B).

Conclusion

Latent HIV-1 reservoir represents the main obstacle in achieving sustained virologic remission in cART treated HIV-1 infected patients following ART treatment interruption.

This is due to two opposing biologic processes occurring in parallel in patients under cART:

1—On the one hand, cART promotes an inhibition of the viral replication triggered by the HIV-1 proviral DNA present in activated peripheral and mucosal reservoir cells. It results from this process a minimal expression of viral particles in the body fluid (<40 copies/ml).

2—On the other hand, the second process is due to the production of type I IFN-α and type III IFN-λ locally, induced by viral replication occurring in these still infected peripheral and mucosal cells, which contain latent integrated HIV proviruses.

By their antiviral effects, these interferons locally reduce the ongoing viral replication occurring in these reservoir cells, which limits the local propagation of the virus to nearby cells but still maintains the reservoir of infected cells.

Figure 7:
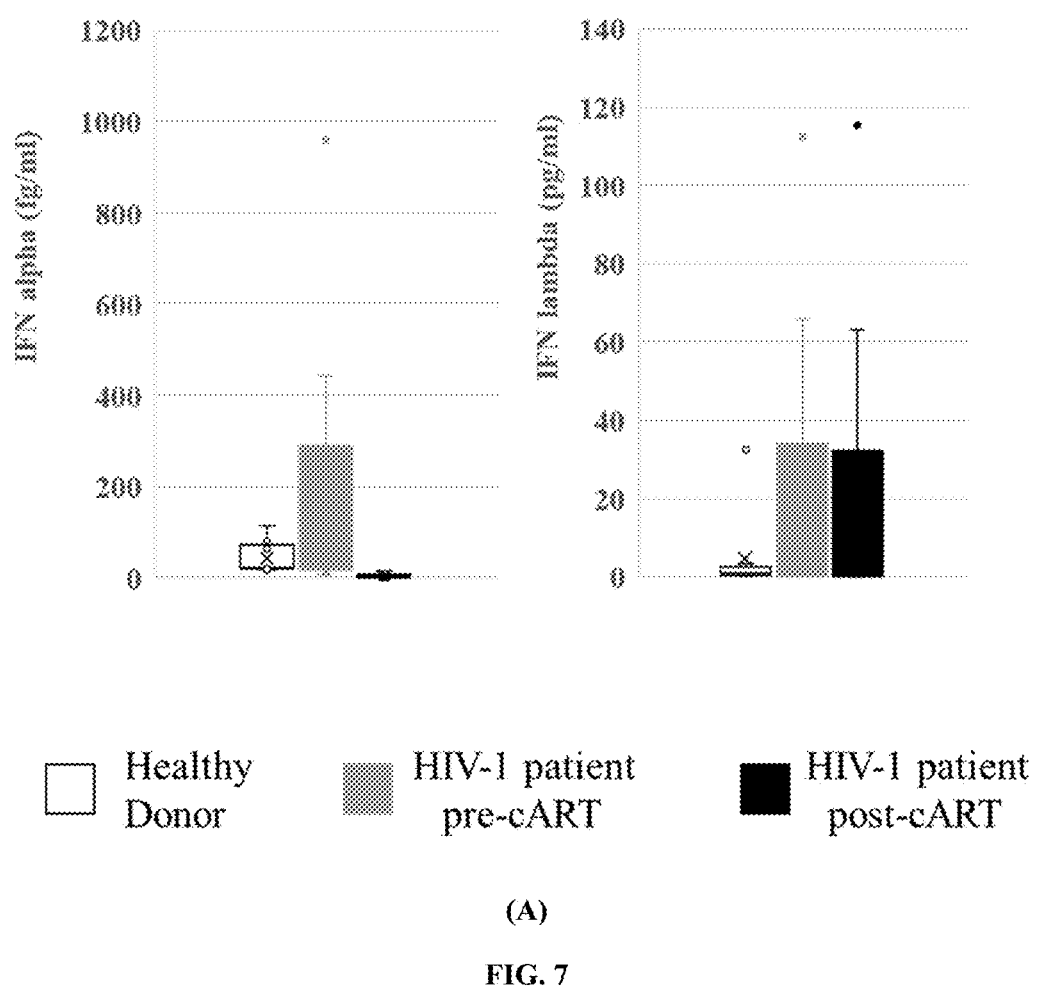
FIG. 7. Serum levels of IFN-α and IFN-λ, before and after cART treatment in HIV-1 patients originating from two distinct institutes ((A) Institute 1; (B) Institute 2) and control healthy donors.
Figure 7:
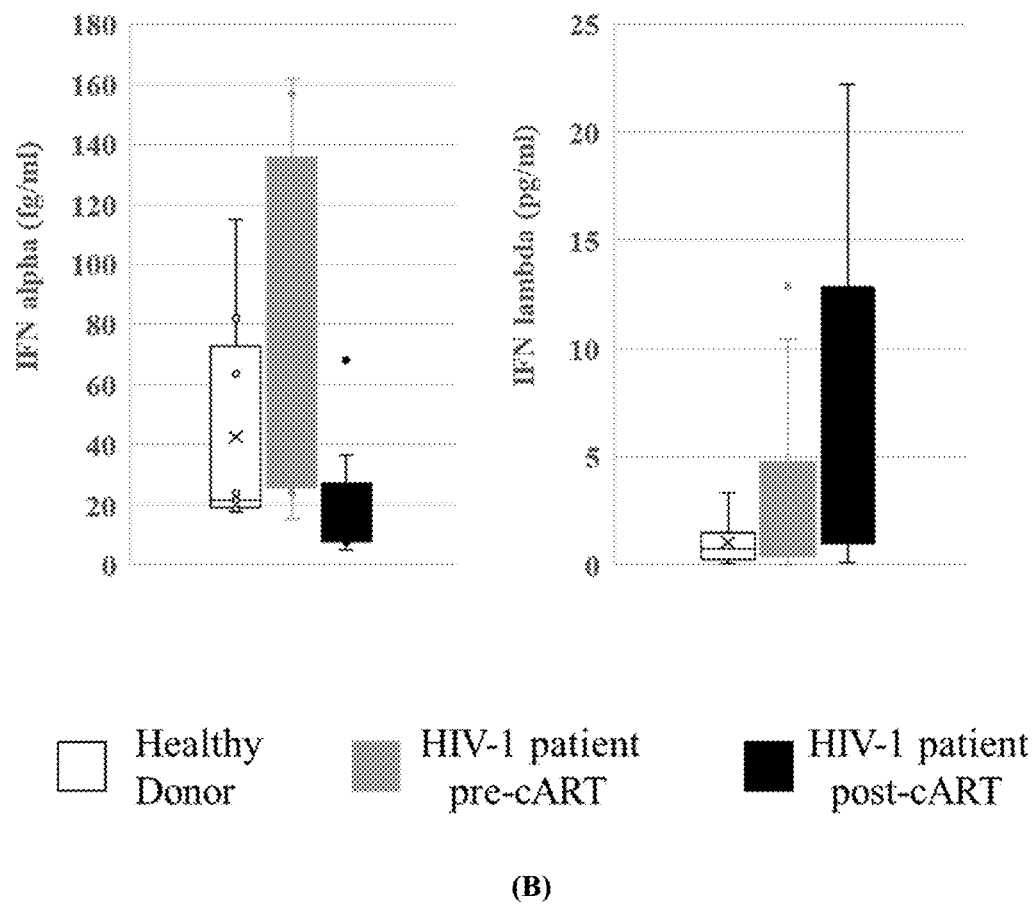

The local production of IFN-α and IFN-λ by peripheral and mucosal cells, which are still infected and replicating the virus, is confirmed by the presence in the serum of post-cART patients of substantial concentrations of these antiviral cytokines (FIG. 7).

Following the blocking of the peripheral and mucosal antiviral interferons, which hinder expression of viral replication in reservoir cells, the HIV-1 proviral DNA present in these reservoir cells may fully replicate viruses. In turn, cART treatment, which controls viral replication, may reduce and progressively eliminate these peripheral and mucosal cellular reservoirs.

Example 3: Clinical Protocol for AIDS Treatment in Human Patients

Study Design

Figure 8:
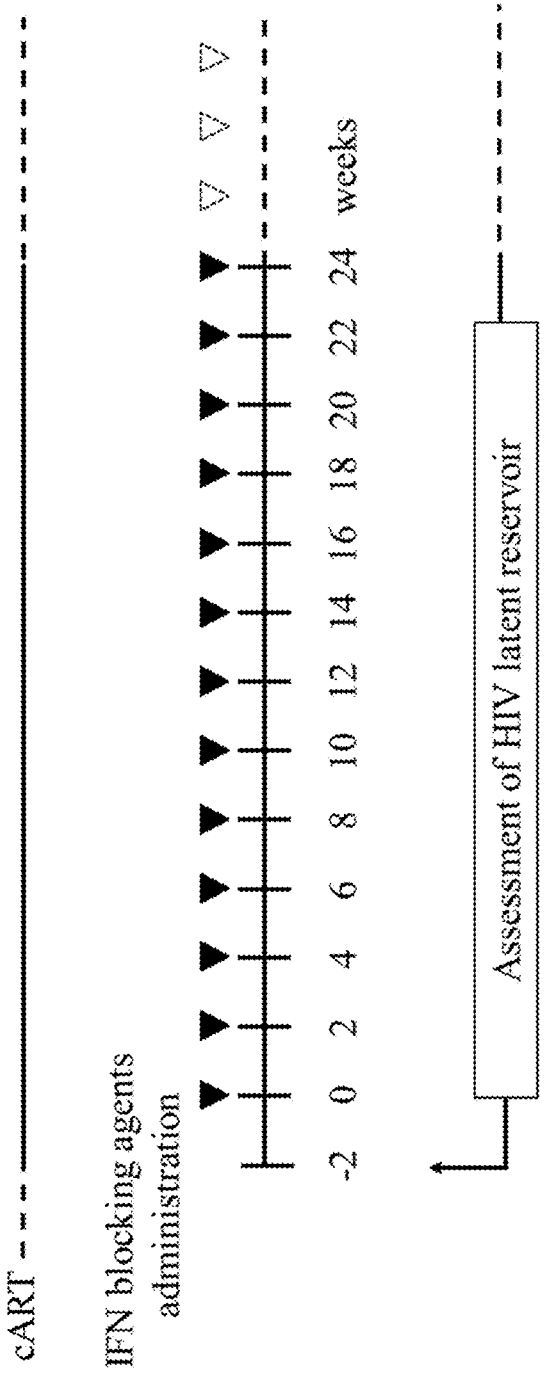
FIG. 8. Schematic diagram of possible administration schedule for the combination of the invention.

Study eligibility criteria includes patients having ongoing ART (>three drugs) with plasma HIV-1 RNA levels <40 copies/ml as well as a CD4$^+$ T cell count >500 cells/µl (and optionally <500 cells/µl). Patients receive infusions of anti-IFN-α, anti-IFN-λ, monoclonal antibodies and optionally anti-IFN-β monoclonal antibodies at 2-week intervals in parallel with their ongoing daily cART therapy (FIG. 8). Plasma HIV-1 RNA levels, size of the reservoir and CD4$^+$ T cell counts are monitored every 2 weeks, after collection of blood samples, 1 day before each mAbs infusion.

Plasma HIV-1 RNA Levels

HIV-1 RNA levels are determined using the Roche COBAS AmpliPrep/COBAS TaqMan HIV-1 Assay (version 2.0) or the Roche cobas HIV-1 quantitative nucleic acid test (cobas 6800), which quantitate HIV-1 RNA over a range of 2×101 to 1×107 copies/ml.

Quantitative Viral Outgrowth Assay

Size of the HIV reservoir is assessed with Quantitative Viral Outgrowth Assay (QVOA) as previously described (Huang et al., 2018, J Clin Invest 128:876-889). Briefly, isolated CD4$^+$ T cells are plated out in serial dilutions (2, 1, 0.5, 0.2, and 0.1 million per well) into 12 wells in a 24-well plates with phytohemagglutinin (PHA; 2 µg/ml) and irradiated HIV-negative donor PBMC (2×10$^6$ cells/well) to reactivate the infected cells. After 2 days of culture, MOLT-4 CCR5 cells (2×10$^6$ cells/well) are added to amplify the HIV. After 2 weeks of culture, p24 antigen is quantified in the culture supernatant, using an HIV p24 antigen enzyme-linked immunosorbent assay (ELISA) kit (Perkin-Elmer, Hopkinton, MA), and estimated frequencies of cells with replication-competent HIV-1 are calculated using limiting dilution analysis.

CD4+ T-Cell Counts

CD4+ T-cell counts are determined by a clinical flow cytometry assay.

Treatment Interruption

Monoclonal antibodies infusion is stopped when no cells with replication-competent HIV-1 are detected following 2-3 consecutive limiting dilution virus outgrowth assays (VOA). Then, ART treatment is stopped when no cells with replication-competent HIV-1 are detected with 3-4 consecutive limiting dilution virus outgrowth assays.

The invention claimed is:

1. A method for inhibiting viral rebound in an ART-treated HIV-1-infected subject having undetectable plasma HIV-1 RNA levels by reducing the proviral level of HIV-1 in latent CD4$^+$ T-cell reservoirs in the subject, said method comprising administering to the subject in need thereof a combination comprising:
   i) a type III interferon blocking agent being an antibody that binds to IFNLR1 being clone MMHLR-1, and chimeric or humanized antibodies derived therefrom,
   ii) interferon-alpha (IFN-α) blocking agent being an antibody that binds to IFNAR1 being Anifrolumab a chimeric or humanized antibody derived therefrom; or an antibody that binds to IFN-α selected from the group consisting of Sifalimumab, Rontalizumab and S95021, and
   iii) antiretroviral therapy (ART) agents comprising:
      two Nucleoside reverse transcriptase inhibitors (NRTIs), and
      at least one agent selected from the group consisting of Protease inhibitor (PI), a Non-nucleoside reverse transcriptase inhibitor (NNRTI), and an Integrase inhibitor (INSTI),
   wherein said subject has already received at least one dose of said antiretroviral therapy (ART) agents before being administered said combination.

2. The method according to claim 1, wherein the antiretroviral therapy (ART) agents further comprise at least one agent selected from the group consisting of Fusion inhibitors (FIs), Chemokine receptor antagonists (CCR5 antagonists) and Entry inhibitors (CD4-directed post-attachment inhibitors).

3. The method according to claim 1, wherein the method further comprises assessing the presence of CD4$^+$ T cells containing replication-competent proviral HIV-1 DNA in a blood sample from the subject.

4. The method according to claim 1, wherein the IFN-α blocking agent, the type III interferon blocking agent, and the antiretroviral therapy (ART) agents are administered simultaneously, separately or sequentially.

5. The method according to claim 1, wherein the IFN-α blocking agent and the type III interferon blocking agent, are administered sequentially.

6. The method according to claim 1, wherein the IFN-α blocking agent and/or the type III interferon blocking agent are administered every week, every 2 weeks or every 3 weeks.

7. The method according to claim 1, wherein the antiretroviral therapy (ART) agents are administered daily.

8. The method according to claim 1, wherein the IFN-α blocking agent and the type III interferon blocking agent are administered parenterally or intravenously.

9. The method according to claim 1, wherein the antiretroviral therapy (ART) agents are administered orally.

10. The method according to claim 1, wherein the subject receives one or more doses of the IFN-α blocking agent of the type III interferon blocking agent before receiving said combination.

11. The method according to claim 1, wherein the subject receives one or more doses of the antiretroviral therapy (ART) agents before receiving said combination.

12. The method according to claim 1, wherein said combination is administered to the subject until the proviral level of HIV 1 in latent CD4$^+$ T cells reservoirs in said subject is reduced down to the proviral HIV 1 CD4$^+$ T cells reservoirs of Elite Controllers.

13. The method according to claim 1, wherein said antiretroviral therapy (ART) agents comprise two Nucleoside reverse transcriptase inhibitors (NRTIs), at least one Non-nucleoside reverse transcriptase inhibitor (NNRTI) and at least one Protease inhibitor (PI).

14. The method according to claim 1, wherein the antiretroviral therapy (ART) agents are administered daily, and wherein the IFN-α blocking agent and/or the type III interferon blocking agent are administered every 3 weeks.

15. The method according to claim 1, wherein said composition further comprises a latency-reversing agent (LRA) selected from the group consisting of HDAC inhibitor romidepsin, PKC agonist bryostatin-1, PKC agonist prostratin, PKC agonist ingenol, TRL7 agonist GS-9620, TLR9 agonist MGN1703, and combinations thereof.

16. The method according to claim 1, wherein the antiretroviral therapy (ART) agents are combined ARTs (cARTs) selected from the group consisting of:
a) emtricitabine (NRTI), tenofovir alafenamide (NRTI), and rilpivirine (NNRTI),
b) emtricitabine (NRTI), tenofovir alafenamide (NRTI), and bictegravir (INSTI),
c) emtricitabine (NRTI), tenofovir disoproxil fumarate (NRTI), and efavirenz (NNRTI), and
d) lamivudine (NRTI), tenofovir (NRTI), and raltegravir (INSTI).

17. The method according to claim 1, wherein said combination is administered to the subject until an amount of intact HIV-1 proviral genomes in said subject is reduced by at least about 20 times compared to an amount of intact HIV-1 proviral genomes in said subject before treatment.

18. The method according to claim 1, wherein said combination is administered to the subject until plasma HIV-1 RNA levels in said subject remains lower than 50 copies/mL in the absence of any ART treatment.

* * * * *